US011992485B2

(12) United States Patent
Worthington

(10) Patent No.: US 11,992,485 B2
(45) Date of Patent: *May 28, 2024

(54) ANALGESIC FORMULATIONS AND METHODS FOR REDUCED POSTOPERATIVE NAUSEA AND VOMITING AND ENHANCED POSTOPERATIVE PAIN RELIEF

(71) Applicant: Hutchison Health, LLC, Laramie, WY (US)

(72) Inventor: William Bradley Worthington, Georgetown, SC (US)

(73) Assignee: HUTCHISON HEALTH, LLC, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/187,407

(22) Filed: Mar. 21, 2023

(65) Prior Publication Data

US 2023/0218601 A1 Jul. 13, 2023

Related U.S. Application Data

(63) Continuation-in-part of application No. 18/187,236, filed on Mar. 21, 2023, which is a continuation-in-part of application No. 18/069,006, filed on Dec. 20, 2022, which is a continuation of application No. 16/834,863, filed on Mar. 30, 2020, now Pat. No. 11,559,521, which is a continuation-in-part of application No. 16/129,026, filed on Sep. 12, 2018, now abandoned, which is a continuation of application No. 14/997,046, filed on Jan. 15, 2016, now Pat. No. 10,098,872, which is a (Continued)

(51) Int. Cl.
| | |
|---|---|
| *A61K 31/445* | (2006.01) |
| *A61K 9/00* | (2006.01) |
| *A61K 31/135* | (2006.01) |
| *A61K 31/137* | (2006.01) |
| *A61K 31/407* | (2006.01) |
| *A61K 31/417* | (2006.01) |
| *A61K 31/4174* | (2006.01) |
| *A61K 31/5415* | (2006.01) |
| *A61K 45/06* | (2006.01) |
| *A61M 25/00* | (2006.01) |
| *A61P 23/02* | (2006.01) |
| *A61P 29/00* | (2006.01) |

(52) U.S. Cl.
CPC .......... *A61K 31/445* (2013.01); *A61K 9/0019* (2013.01); *A61K 31/135* (2013.01); *A61K 31/137* (2013.01); *A61K 31/407* (2013.01); *A61K 31/417* (2013.01); *A61K 31/4174* (2013.01); *A61K 31/5415* (2013.01); *A61K 45/06* (2013.01); *A61M 25/0068* (2013.01); *A61K 2300/00* (2013.01); *A61P 23/02* (2018.01); *A61P 29/00* (2018.01)

(58) Field of Classification Search
CPC ..... A61K 31/445; A61K 31/135; A61P 23/02; A61P 29/00
See application file for complete search history.

(56) References Cited

U.S. PATENT DOCUMENTS

| 8,992,951 B2 | 3/2015 | Henry |
| 10,143,685 B2 | 12/2018 | Berkheimer |

(Continued)

FOREIGN PATENT DOCUMENTS

| CA | 3111570 A1 * | 3/2020 | ........... A61K 31/445 |
| CA | 3111570 A1 | 3/2020 | |

(Continued)

OTHER PUBLICATIONS

Sahar Abdel-Baky Mohamed et al., Pain Physician 2016; 19:E829-E839. (Year: 2016).*
Erdivanli et al., Rev Bras Anestesiol. 2013, 63(2), pp. 183-187. (Year: 2013).*
Santos et al, 1998, vol. 47, pp. 302-307. (Year: 1998).*
Ilkjaer et al, British Journal of Anesthesia1996, vol. 76, 829-834. (Year: 1996).*
Kawamura et al., Drug Delivery System 2003, vol. 18(5), pp. 459-470). (Year: 2003).*
Vahabi et al., HK J Paedtr 2012, vol. 17, pp. 109-114. (Year: 2012).*
Webpage printout of NCBI Bookshelf, Physiology, Nociceptive Pathways, https://www.ncbi.nlm.nih.gov/books/NBK470255/, pp. 1-4, Accessed Nov. 29, 2023 (Year: 2023).*
Brockway, et al. "Comparison of extradural ropivacaine and bupivacaine." British Journal of Anaesthesia 66.1 (1991): 31-37.

(Continued)

Primary Examiner — Craig D Ricci
Assistant Examiner — Janet L Coppins
(74) Attorney, Agent, or Firm — NGUYEN TARBET LLC

(57) ABSTRACT

Opioid-free, anesthetic, analgesic, analgesic, anti-nociceptive, anti-inflammatory, antiemetic formulations, and methods for reducing pain, controlling pain, preventing pain, reducing or eliminating exposure to opioids, decreasing nausea and vomiting, featuring administration of the anesthetic/analgesic formulations. The opioid-free/sparing anesthetic/analgesic formulations comprise a local anesthetic, a cyclooxygenase (COX) inhibitor, and an alpha agonist. The formulations may optionally comprise additional compositions including but not limited to NMDA receptor antagonists, Buprenorphine, Dexketoprofen, Carprofen, an antifibrinolytic, an antibiotic, a steroid, a cyclooxygenase 3 inhibitor, a Transient Receptor Potential Vanilloid (TRPV) receptor agonist or antagonist, a protein kinase inhibitor, a competitive or non-competitive glycine or glutamate agonist, a glutamate or glycine inhibitor or antagonist, a neurokinin-1 receptor antagonist, an alpha agonist, a second alpha agonist, and combinations thereof. The formulations are effective for significantly reducing postoperative nausea and vomiting and enhancing postoperative pain relief as compared to existing prior art anesthetics/analgesics.

1 Claim, No Drawings

Related U.S. Application Data continuation-in-part of application No. 14/337,819, filed on Jul. 22, 2014, now abandoned.

(60) Provisional application No. 61/856,979, filed on Jul. 22, 2013.

(56) References Cited

U.S. PATENT DOCUMENTS

| | | |
|---|---|---|
| 10,952,963 B2 | 3/2021 | Leeah et al. |
| 2004/0265364 A1 | 12/2004 | Ozturk et al. |
| 2019/0314278 A1 | 10/2019 | Leeah et al. |

FOREIGN PATENT DOCUMENTS

| | | | |
|---|---|---|---|
| EP | 0799051 B1 | 7/2004 | |
| EP | 2117521 B1 * | 6/2012 | ........... A61K 31/445 |
| WO | 2012054831 A2 | 4/2012 | |

OTHER PUBLICATIONS

Worthington, Memorandum: Experimental Use Exception & Non-Obviousness; Jan. 22, 2018.
Worthington, "Analgesic formulations and methods for reduced postoperative nausea and vomiting and enhanced postoperative pain relief."; 2018.
Worthington, Tables 1. Patel prior art Study PONV, Table 2. Wang and Rahmanian prior arts Study in Pain Relief, Table 3. Worthington prior art in Pain Relief; 2018.
Sveticic et al. "Combinations of morphine with ketamine for patient-controlled analgesia: a new optimization method." The Journal of the American Society of Anesthesiologists 98.5 (2003): 1195-1205.
Ya Deau, et al. "Similar analgesic effect after popliteal fossa nerve blockade with 0.375% and 0.75% bupivacaine." HSS Journal® 3.2 (2007): 173-176.
Patel et al. "Comparative study of bupivacaine vs bupivacaine and ketamine (Intrathecally) during intraoperative and post operative analgesia in non PIH caesarian section." National Journal of Medical Research 1.02 (2011): 71-75.
Pierre, Sébastien, and Rachel Whelan. "Nausea and vomiting after surgery." Continuing Education in Anaesthesia, Critical Care & Pain 13.1 (2013): 28-32.
Gan et al. "Consensus guidelines for the management of postoperative nausea and vomiting." Anesthesia & Analgesia 118.1 (2014): 85-113.
Koivuranta et al. "A survey of postoperative nausea and vomiting." Anaesthesia 52.5 (1997): 443-449.
Shaikh et al. "Pain, nausea, vomiting and ocular complications delay discharge following ambulatory microdiscectomy." Canadian Journal of Anesthesia 50.5 (2003): 514.
Cruthirds, Danielle, Pamela J. Sims, and Patrick J. Louis. "Review and recommendations for the prevention, management, and treatment of postoperative and postdischarge nausea and vomiting." Oral surgery, oral medicine, oral pathology and oral radiology 115.5 (2013): 601-611.
Bion, J. F. "Intrathecal ketamine for war surgery. A preliminary study under field conditions." Anaesthesia 39.10 (1984): 1023-1028.
Kathirvel et al. "Effects of intrathecal ketamine added to bupivacaine for spinal anaesthesia." Anaesthesia 55.9 (2000): 899-904.
Apfelbaum et al. "Postoperative pain experience: results from a national survey suggest postoperative pain continues to be undermanaged." Anesthesia & Analgesia 97.2 (2003): 534-540.
Gan et al. "Incidence, patient satisfaction, and perceptions of post-surgical pain: results from a US national survey." Current medical research and opinion 30.1 (2014): 149-160.
Wang et al. "Intrathecal ketorolac does not improve acute or chronic pain after hip arthroplasty: a randomized controlled trial." Journal of anesthesia 28 (2014): 790-793.
Rahmanian et al. "The effects of bupivacaine on postoperative back pain after lumbar laminectomy: a randomized clinical trial." Neurosurgery Quarterly 26.4 (2016): 293-297.
LeBlanc et al. "Evaluation of continuous infusion of 0.5% bupivacaine by elastomeric pump for postoperative pain management after open inguinal hernia repair." Journal of the American College of Surgeons 200.2 (2005): 198-202.
Misiolek et al. "The 2014 guidelines for post-operative pain management." Anaesthesiol Intensive Ther 46.4 (2014): 221-244.
Misiolek et al. "The 2014 guidelines for post-operative pain management." Anaesthesiol Intensive Ther 46.4 (2014): 221-244.
Ikeuchi et al. "Effects of dexamethasone on local infiltration analgesia in total knee arthroplasty: a randomized controlled trial." Knee Surgery, Sports Traumatology, Arthroscopy 22 (2014): 1638-1643.
Guo et al. "The preemptive analgesic effect of capsaicin involves attenuations of epidermal keratinocytes proliferation and expression of pro-inflammatory mediators after plantar incision in rats." Journal of Pain Research (2023): 141-149.
Teichman, Sam. Poster: Vocacapsaicin Reduces Pain and Opioid Consumption for Two Weeks Following a Single Administration During Total Knee Arthroplasty.
Concentric Analgesics Announces Podium Presentation of Vocacapsaicin Clinical Data at 46th Annual ASRA Meeting, Retrieved Aug. 9, 2023 https://www.concentricanalgesics.com/concentric-analgesics-announces-podium-presentation-of-vocacapsaicin.
Mohamed, Sahar Abd-Elbaky, Ahmad Mohammad Abd El-Rahman, and Khaled M. Fares. "Intrathecal dexmedetomidine, ketamine, and their combination added to bupivacaine for postoperative analgesia in major abdominal cancer surgery." Pain Physician 19.6 (2016): E829.
Goldstein et al. Intraperitoneal instillation of bupivacaine or ropivacaine reduces pain and postoperative nausea and vomiting. Inpharma Wkly. 1253, 13 (2000).
Moore, R. Andrew, and Jodie Barden. "Systematic review of dexketoprofen in acute and chronic pain." BMC clinical pharmacology 8.1 (2008): 1-11.

\* cited by examiner

ANALGESIC FORMULATIONS AND METHODS FOR REDUCED POSTOPERATIVE NAUSEA AND VOMITING AND ENHANCED POSTOPERATIVE PAIN RELIEF

CROSS REFERENCE

This application is a continuation-in-part and claims benefit of U.S. patent application Ser. No. 18/187,236 filed Mar. 21, 2023, which is continuation-in-part and claims benefit of U.S. patent application Ser. No. 18/069,006 filed Dec. 20, 2022, which is a continuation and claims benefit of U.S. patent application Ser. No. 16/834,863 filed Mar. 30, 2020 now U.S. Pat. No. 11,559,521, issued Jan. 24, 2023, which is a continuation-in-part and claims benefit of U.S. patent application Ser. No. 16/129,026, filed Sep. 12, 2018, which is a continuation and claims benefit of U.S. patent application Ser. No. 14/997,046, filed Jan. 15, 2016, now U.S. Pat. No. 10,098,872, issued Oct. 16, 2018, which is a continuation-in-part and claims benefit of U.S. patent application Ser. No. 14/337,819, filed Jul. 22, 2014, which is a Non-Provisional and claims benefit of U.S. Provisional Patent Application No. 61/856,979, filed Jul. 22, 2013, the specification(s) of which is/are incorporated herein in their entirety by reference.

FIELD OF THE INVENTION

The present invention relates to multimodal opioid-free, opioid-sparing analgesic formulations for preventing pain, for pain management and anti-emesis, including but not limited to postoperative pain.

BACKGROUND OF THE INVENTION

The treatment and relief of pain is one of the most common reasons patients seek medical evaluation. Pain has been defined by the International Association for the Study of Pain as the response to real or perceived tissue trauma. The word "pain" derives from the Latin "poena," or punishment. Postoperative pain is an example of acute pain. During the perioperative period, clinicians focus attention on helping abolish pain and discomfort associated with noxious stimuli and associated surgical tissue trauma. It is now recognized that many current modalities used to treat acute postoperative pain are incomplete and/or cause significant treatment related conditions, such as opioid related adverse drug effects. The current opioid crisis is an example, where opioids used for unimodal post-operative pain management give rise to significant immediate and chronic opioid related adverse effects, morbidity, and mortality.

Surgical pain causes a generalized and biphasic response. The first response due to direct surgical trauma produces transduction of nociceptive afferent input via c-fiber and a-delta neuronal activation leading to transmission, modulation and perception of pain signals in the peripheral and central nervous system. At the time of surgical trauma, complex inflammatory processes are triggered, leading to further afferent noxious input, causing peripheral and secondary central nociceptive sensitization. This results in a reduction in the stimulation threshold of surrounding nociceptors with increased excitation and recruitment of nociceptive afferents known as wind up neuroplasticity.

Surgical trauma results in a complex local release of inflammatory mediators further contributing to peripheral sensitization and recruitment of higher threshold nociceptors, giving rise to secondary hyperalgesia. where non-painful stimuli like light touch are perceived as painful.

Central sensitization refers to processes occurring at the spinal dorsal root ganglion, dorsal horn, and higher regions of the central nervous system in response to ongoing afferent nociceptor barrage. This leads to an expansion of the nociceptive field size, increased and magnified response to nociceptive stimuli, and a reduction in the afferent stimuli threshold that is perceived as painful.

It is well known in the literature that anesthetic induced postoperative nausea and vomiting (PONV) is the most common adverse drug effect in the immediate perioperative period. Gan T. J. et al. and M. Koivuranta et al., reported that of the patients undergoing general anesthesia, between 30% to 50% of patients suffer from PONV and this rate can increase to 80% in a high-risk subset in patients undergoing general anesthesia, including those patients treated with opioids, over a 24-hour period postoperatively. Therefore, there remains an unmet need for clinically and statistically significant enhanced methods and improvements, improving analgesia, improving, or eliminating PONV compared to standard of care therapies.

BRIEF SUMMARY OF THE INVENTION

The present invention features multimodal opioid-free, opioid-sparing analgesic (MMOSA) formulations that define and provide opioid-free/sparing analgesia by modulating molecular and cellular mechanisms of nociception. As will be described herein, the formulations are effective for significantly reducing postoperative nausea and vomiting and enhance postoperative pain relief as compared to existing prior art anesthetics/analgesics. Without wishing to limit the present invention to any theory or mechanism, it is believed that the formulations of the present invention are advantageous because they feature drugs that, in synergism, provide long-lasting effects that are opioid-free and antiemetic.

As used herein, the formulations herein may be referred to as "multimodal opioid-sparing analgesic" formulations, or "MMOSA" formulations. A non-limiting example of a MMOSA formulation includes the "BKK" formulation, as is described below. The present invention is not limited to the specific BKK example of MMOSA formulations.

The present invention features methods of treating pain and reducing nausea and vomiting. In some embodiments, the method comprises administering, by subcutaneous injection, rectal injection or retention, intramuscular injection, interfascial plane injection, tumescent or intraperitoneal injection, nebulization, transdermal delivery, or intradermal injection, a clinically effective amount of a formulation to a mammal in need of such treatment, wherein the formulation comprises about 0.01%-0.5% of a local anesthetic comprising Bupivacaine Hydrochloride, Ropivacaine Hydrochloride, or Levobupivacaine Hydrochloride, about 0.01-1.5 mg/cc of a cyclooxygenase (COX) inhibitor comprising Meloxicam, Ketorolac Tromethamine, Ibuprofen, Acetaminophen, Diclofenac, Parecoxib, Ketoprofen, Dexketoprofen, Carprofen, Celecoxib, Naproxen, Tolmetin, Etodolac, Fenoprofen, Indomethacin, Diflunisal, or Nabumetone, and about 0.0001-0.05 mg/cc of an alpha agonist comprising Epinephrine, Clonidine, or Dexmedetomidine.

In some embodiments, the formulation further comprises: Buprenorphine, Methadone, Dexketoprofen, Carprofen, an N-methyl-D-aspartate (NMDA) receptor antagonist, an antifibrinolytic, an antibiotic, a steroid, a cyclooxygenase 3 inhibitor, a Transient Receptor Potential Vanilloid (TRPV)

receptor agonist or antagonist, a Transient Receptor Potential channel agonist or antagonist, a protein kinase inhibitor, a competitive or non-competitive glycine or glutamate agonist, a glutamate or glycine inhibitor, a neurokinin-1 receptor antagonist, an alpha agonist, a second alpha agonist, or a combination thereof.

In some embodiments, the NMDA receptor antagonist is Magnesium Sulfate, Ketamine Hydrochloride, Trolamine, Tramadol, Ifenprodil, Dextromethorphan, Meperidine, Methadone, Minocycline, Agmatine, or Aptiganel. In some embodiments, the antifibrinolytic is Tranexamic Acid, Epsilon-aminocaproic acid, or a lysine analog, Aprotinin, or a serine protease inhibitor. In some embodiments, the alpha agonist is Epinephrine, and the second alpha agonist is Clonidine, Dexmedetomidine, Tizanidine, Phenylephrine, Guanfacine, or Medetomidine. In some embodiments, the cyclooxygenase 3 inhibitor is Acetaminophen or Paracetamol. In some embodiments, the steroid is Dexamethasone, Methylprednisolone, Betamethasone, Diprospan, a mineralocorticosteroid, or a glucocorticosteroid. In some embodiments, the antibiotic is a beta lactam ring antibiotic or Vancomycin. In some embodiments, the Transient Receptor Potential channel agonist or antagonist is Magnesium Sulfate, Remacemide, Tiletamine, Capsaicin, Resiniferatoxin, Vocacapsaicin, Cinnamaldehyde, Capsazepine, an aryl urea cinnamide, a carboxamide antagonist, or a vanilloid agonist or antagonist. In some embodiments, the protein kinase inhibitor is Temsirolimus, PKA, mTOR, MAPK, PKG, p38 MAPKs, EGFR, PKG, ERK, JAK, a tropomyosin related kinase inhibitor (TrK), BDNF, VEGFR, or a combination thereof.

In some embodiments, the formulation is administered to a site prior to a needle insertion or an incision. In some embodiments, the formulation is administered during, before, or after: any surgical incision, laceration, or pre- or post-endoscopic port site, total joint procedures, anterior spinal procedures, posterior spinal procedures, Lumbar Discectomies, Decompressive Lumbar Laminectomies, Anterior Cervical Discectomies, Peripheral Nerve Decompressive Procedures, Anterior Lumbar Discectomy or Fusion, Decompressive Laminectomy with/or without instrumentation, Cardiovascular surgery, pacemaker insertion, defibrillator insertion, Colorectal surgery, General surgery, Gynecological and Obstetrical surgery, Neurological surgery, Ophthalmic surgery, Orthopedic surgery, Oral Maxillofacial surgery, Otolaryngologic surgery, Pediatric surgery, Dental procedures and surgery, Podiatric surgery, Endoscopic surgery, a laceration, a surgical incision, a neurosurgical procedure on the cranium, spine, or extremities, an open decompressive procedure on peripheral nerves, spinal nerves and spinal plexuses, or lamina, including fusions an instrumentation, an orthopedic application, open reduction, internal fixation of fractures, closed reduction of fractures, direct injection of hematoma, total joint arthroplasty of the shoulder, knee, hip, elbow, or ankle, a general surgery procedure, hepatobiliary surgery, robotic laparoscopic assisted or laparoscopic cholecystectomy, appendectomy, colectomy, hernia repair, hemorrhoidectomy, breast surgeries, excision, biopsy, augmentation or reduction, amputations of extremities or digits. Cardiothoracic surgery, thoracotomy, mediastinal surgery, sternotomy and robotic or video assisted thoracoscopy, an otolaryngological procedure, a dental procedure, maxillofacial surgery, a surgery on the neck or throat, ear surgery, thyroid or parathyroid surgery, tonsillectomy, adenoidectomy, laryngectomy, third molar extraction, temporomandibular joint surgery, a dental extraction or endodontic procedure, dental implant surgery, hysterectomy, oophorectomy, C-section, robotic assisted and/or laparoscopic or laparotomy surgery, bunionectomy, forefoot surgery, hind foot surgery, plantar surgery, foot or ankle joint arthroplasty, Veterinary surgery or procedures, a minimally invasive or open surgical incision or traumatic laceration, fracture or open wound, or any applicable and appropriate animal or human surgery or procedure.

In some embodiments, the formulation is administered via an elastomeric or electronic pump, syringe, or an active or passive transdermal delivery system. In some embodiments, the formulation is administered via a nebulizer.

The present invention also features a method of treating pain and reducing nausea and vomiting, wherein the method comprises administering, by subcutaneous injection, intramuscular injection, Interfacial plane injection, rectal infiltration or retention, transdermal delivery, intradermal injection, tumescent or intra-peritoneal infiltration, a clinically effective amount of a formulation to a mammal in need of such treatment, wherein the formulation comprises about 0.01%-0.5% of a local anesthetic comprising Bupivacaine Hydrochloride, Ropivacaine Hydrochloride, Levobupivacaine Hydrochloride, Lidocaine, Prilocaine, Amethocaine, Procaine, Cinchocaine, Mepivacaine, Etidocaine, or Tetracaine, about 0.01-1.5 mg/cc of a cyclooxygenase (COX) inhibitor comprising Meloxicam, Ketorolac Tromethamine, Dexketoprofen, Ibuprofen, Acetaminophen, Diclofenac, Parecoxib, Ketoprofen, Celecoxib, Naproxen, Tolmetin, Etodolac, Fenoprofen, Indomethacin, Diflunisal, Carprofen, or Nabumetone, and about 0.001-0.05 mg/cc of an alpha agonist comprising Epinephrine, Clonidine, Phenylephrine, or Dexmedetomidine.

In some embodiments, the formulation further comprises: Buprenorphine, Methadone, Dexketoprofen, Carprofen, an N-methyl-D-aspartate (NMDA) receptor antagonist, an antifibrinolytic, an antibiotic, a steroid, a cyclooxygenase 3 inhibitor, a Transient Receptor Potential Vanilloid (TRPV) receptor agonist or antagonist, a Transient Receptor Potential channel agonist or antagonist, a protein kinase inhibitor, a competitive or non-competitive glycine or glutamate agonist, a glutamate or glycine inhibitor, a neurokinin-1 receptor antagonist, an alpha agonist, a second alpha agonist, or a combination thereof.

In some embodiments, the NMDA receptor antagonist is MgSO4, Ketamine Hydrochloride, Trolamine, Tramadol, Ifenprodil, Dextromethorphan, Meperidine, Methadone, Minocycline, Agmatine, or Aptiganel. In some embodiments, the antifibrinolytic is Tranexamic Acid, Epsilon-aminocaproic acid, or another lysine analog, Aprotinin, or a serine protease inhibitor. In some embodiments, the cyclooxygenase 3 inhibitor is Acetaminophen or Paracetamol. In some embodiments, the steroid is Dexamethasone, Methylprednisolone, Betamethasone, Diprospan, a mineralocorticosteroid, or a glucocorticosteroid.

The present invention also features compositions for treating and modulating mechanisms of nociception and for administering by subcutaneous injection, intramuscular injection, interfascial plane injection, transdermal delivery, tumescent or intraperitoneal or intradermal injection. In some embodiments, the composition comprises about 0.01%-0.5% of a local anesthetic comprising Bupivacaine Hydrochloride, Ropivacaine Hydrochloride, Levobupivacaine Hydrochloride, Lidocaine, Prilocaine, Amethocaine, Procaine, Cinchocaine, Mepivacaine, Etidocaine, or Tetracaine; about 0.01-3.0 mg/cc of an N-methyl-D-aspartate (NMDA) receptor antagonist comprising Magnesium Sulfate, Methadone, Ketamine Hydrochloride, Trolamine, Tramadol, Ifenprodil, Dextromethorphan, Meperidine, Minocycline, Agmatine, or Aptiganel; and about 0.01-1.5 mg/cc of a cyclooxygenase (COX) inhibitor comprising Meloxicam, Ketorolac Tromethamine, Ibuprofen, Acetaminophen, Diclofenac, Parecoxib, Ketoprofen, Celecoxib, Naproxen, Tolmetin, Etodolac, Fenoprofen, Indomethacin, Diflunisal, Carprofen, Dexketoprofen, or Nabumetone.

In some embodiments, the formulation further comprises: Buprenorphine, Methadone, Dexketoprofen, an antifibrinolytic, an antibiotic, a steroid, a cyclooxygenase 3 inhibitor, a Transient Receptor Potential Vanilloid (TRPV) receptor agonist or antagonist, a Transient Receptor Potential channel agonist or antagonist, a protein kinase inhibitor, a competitive or non-competitive glycine or glutamate agonist, a glutamate or glycine inhibitor, a neurokinin-1 receptor antagonist, an alpha agonist, a second alpha agonist, or a combination thereof.

In some embodiments, the alpha agonist is Clonidine, Dexmedetomidine, Tizanidine, Phenylephrine, Guanfacine, Medetomidine, or Epinephrine. In some embodiments, the alpha agonist is at a concentration of about 0.0001-0.05 mg/cc. In some embodiments, the antifibrinolytic is Tranexamic Acid, Epsilon-aminocaproic acid, or a lysine analog, Aprotinin, or a serine protease inhibitor. In some embodiments, the cyclooxygenase 3 inhibitor is Acetaminophen or Paracetamol. In some embodiments, the steroid is Dexamethasone, Methylprednisolone, Betamethasone, Diprospan, a mineralocorticosteroid, or a glucocorticosteroid. In some embodiments, the antibiotic is a beta lactam antibiotic or Vancomycin. In some embodiments, the Transient Receptor Potential channel agonist or antagonist is Magnesium, Remacemide, Tiletamine, Capsaicin, Resiniferatoxin, Capsazepine, an aryl urea cinnamide, a carboxamide antagonist, or a vanilloid agonist or antagonist. In some embodiments, the protein kinase inhibitor is Temsirolimus, PKA, mTOR, MAPK, PKG, p38 MAPKs, EGFR, PKG, ERK, JAK, a tropomyosin related kinase inhibitor (TrK), BDNF, VEGFR, or a combination thereof.

In some embodiments, the formulation further comprises a buffer consisting of saline solution.

The present invention also features methods of treating and modulating mechanisms of nociception. In some embodiments, the method comprises administering by subcutaneous injection, transdermal delivery, intramuscular injection, interfascial plane injection, tumescent or intraperitoneal or intradermal injection, a clinically effective amount of a formulation to a mammal in need of such treatment, wherein the formulation comprises about 0.01%-0.5% of a local anesthetic comprising Bupivacaine Hydrochloride, Ropivacaine Hydrochloride, Levobupivacaine Hydrochloride, Lidocaine, Prilocaine, Amethocaine, Procaine, Cinchocaine, Mepivacaine, Etidocaine, or Tetracaine; about 0.01-3.0 mg/cc of an N-methyl-D-aspartate (NMDA) receptor antagonist comprising Magnesium Sulfate, Ketamine Hydrochloride, Trolamine, Tramadol, Ifenprodil, Dextromethorphan, Meperidine, Minocycline, Agmatine, or Aptiganel; and about 0.01-1.5 mg/cc of a cyclooxygenase (COX) inhibitor comprising Meloxicam, Ketorolac Tromethamine, Ibuprofen, Acetaminophen, Diclofenac, Parecoxib, Ketoprofen, Celecoxib, Naproxen, Tolmetin, Etodolac, Fenoprofen, Indomethacin, Diflunisal, Carprofen, Dexketoprofen, or Nabumetone.

In some embodiments, the formulation further comprises: Buprenorphine, Methadone, Dexketoprofen, an antifibrinolytic, an antibiotic, a steroid, a cyclooxygenase 3 inhibitor, a Transient Receptor Potential Vanilloid (TRPV) receptor agonist or antagonist, a Transient Receptor Potential channel agonist or antagonist, a protein kinase inhibitor, a competitive or non-competitive glycine or glutamate agonist, a glutamate or glycine inhibitor, a neurokinin-1 receptor antagonist, an alpha agonist, a second alpha agonist, or a combination thereof. In some embodiments, the alpha agonist is Clonidine, Dexmedetomidine, Tizanidine, Phenylephrine, Guanfacine, Medetomidine, or Epinephrine.

In some embodiments, the antifibrinolytic is Tranexamic Acid, Epsilon-aminocaproic acid, or a lysine analog, Aprotinin, or a serine protease inhibitor; the cyclooxygenase 3 inhibitor is Acetaminophen or Paracetamol; the steroid is Dexamethasone, Methylprednisolone, Betamethasone, Diprospan, a mineralocorticosteroid, or a glucocorticosteroid; the antibiotic is a beta lactam antibiotic or Vancomycin; the Transient Receptor Potential channel agonist or antagonist is Magnesium, Remacemide, Tiletamine, Capsaicin, Resiniferatoxin, Capsazepine, an aryl urea cinnamide, a carboxamide antagonist, or a vanilloid agonist or antagonist; or the protein kinase inhibitor is Temsirolimus, PKA, mTOR, MAPK, PKG, p38 MAPKs, EGFR, PKG, ERK, JAK, a tropomyosin related kinase inhibitor (TrK), BDNF, VEGFR, or a combination thereof.

In some embodiments, the formulation is administered during, before, or after: any surgical incision, laceration, or pre- or post-endoscopic port site, total joint procedures, anterior spinal procedures, posterior spinal procedures, Lumbar Discectomies, Decompressive Lumbar Laminectomies, Anterior Cervical Discectomies, Peripheral Nerve Decompressive Procedures, Anterior Lumbar Discectomy or Fusion, Decompressive Laminectomy with/or without instrumentation, Cardiovascular surgery, pacemaker insertion, defibrillator insertion, Colorectal surgery, General surgery, Gynecological and Obstetrical surgery, Neurological surgery, Ophthalmic surgery, Orthopedic surgery, Oral Maxillofacial surgery, Otolaryngologic surgery, Pediatric surgery, Dental procedures and surgery, Podiatric surgery, Endoscopic surgery, a laceration, a surgical incision, a neurosurgical procedure on the cranium, spine, or extremities, an open decompressive procedure on peripheral nerves, spinal nerves and spinal plexuses, or lamina, including fusions an instrumentation, an orthopedic application, open reduction, internal fixation of fractures, closed reduction of fractures, direct injection of hematoma, total joint arthroplasty of the shoulder, knee, hip, elbow, or ankle, a general surgery procedure, hepatobiliary surgery, robotic laparoscopic assisted or laparoscopic cholecystectomy, appendectomy, colectomy, hernia repair, hemorrhoidectomy, breast surgeries, excision, biopsy, augmentation or reduction, amputations of extremities or digits. Cardiothoracic surgery, thoracotomy, mediastinal surgery, sternotomy and robotic or video assisted thoracoscopy, an otolaryngological procedure, a dental procedure, maxillofacial surgery, a surgery on the neck or throat, ear surgery, thyroid or parathyroid surgery, tonsillectomy, adenoidectomy, laryngectomy, third molar extraction, temporomandibular joint surgery, a dental extraction or endodontic procedure, dental implant surgery, hysterectomy, oophorectomy, C-section, robotic assisted and/or laparoscopic or laparotomy surgery, bunionectomy, forefoot surgery, hind foot surgery, plantar surgery, foot or ankle joint arthroplasty, Veterinary surgery or procedures, a minimally invasive or open surgical incision or traumatic laceration, fracture or open wound, or any applicable and appropriate animal or human surgery or procedure.

In some embodiments, the formulation is administered to a site prior to or after a needle insertion or an incision. In some embodiments, the formulation is administered via an elastomeric or electronic pump or syringe. In some embodiments, the formulation is administered with an active transdermal delivery system. In some embodiments, the formulation is administered via a nebulizer.

Any feature, or combination of features, described herein are included within the scope of the present invention provided that the features included in any such combination are not mutually inconsistent as will be apparent from the context, this specification, and the knowledge of one of ordinary skill in the art. Additional clinical patient and patient safety advantages and unexpected innovative aspects of the present invention are apparent in the following detailed description and claims.

Terms

As used herein, "treating" or "treatment" of a disease includes but is not limited to: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As defined herein, an "effective amount" means the amount of a compound that, when administered to a mammal for treating a disease, is sufficient to result in such treatment for the disease. The "effective amount" will vary depending on the formulation, the disease and its severity and the age, weight, pharmacokinetics, and pharmacodynamics of the mammal to be treated.

As defined herein, the term "agonist" refers to an admixture component that enhances a response. The agonist binds to the same site as the endogenous compound or an admixture component and produces the same type of signal, usually of equal or greater magnitude than the endogenous agent. As defined herein, the term "antagonist" refers to an admixture component that diminishes a response. The antagonist binds to the same site as the endogenous compound and diminishes or blocks the signal generated by the endogenous agent. As defined herein, the term "inhibitor" refers to an agent that slows or interferes with a chemical reaction, or a substance that reduces the activity of another substance.

As used herein, the term "admixture" refers to a mixture, mix, combination amalgamation, amalgam, union, conjunction, merging, compound, alloy, fusion, meld, composite, synthesis, homogenization, or something mixed with something else. For example, the present invention features an admixture or a combination comprising specific proportions of an anesthetic, an NMDA-receptor antagonist, and a cyclooxygenase inhibitor. Another example includes an admixture or a combination comprising a local anesthetic, a COX inhibitor, and at least one alpha agonist.

As used herein, the term "multimodal" refers to being characterized by several different concurrent and simultaneous mechanisms of action. For example, the present invention features a formulation that provides multimodal pharmacologic actions comprising anesthetic, analgesic, analgesic, anti-inflammatory, anti-hyperalgesic, non-opioid, and anti-emetic mechanisms of action. In some embodiments, multimodal analgesia is defined by the use of several different drugs or drug classes, unique innovative formulations, with different analgesic mechanisms of action, interfering with nociceptive neuronal transduction, transmission, modulation, and perception of pain.

As used herein, the term "formulation" refers to a material or mixture prepared according to a formula or putting together components in appropriate relationships or structures, according to a formula. For example, the present invention features a formulation comprising specific amounts of specific compounds that collectively and independently provide multimodal mechanisms of analgesia, anti-inflammation, antalgesia, and anti-emesis comprising specific amounts of at least three or more compounds or drug classifications.

As used herein "NMDARA" is an NMDA (N-methyl D-aspartate) receptor antagonist (NMDARA), such as Ketamine (Ketamine Hydrochloride), Trolamine, Tramadol, Dextromethorphan, Meperidine, or Minocycline, Agmatine, Magnesium Sulfate, Aptiganel, Ifenprodil, or any other competitive or non-competitive N-methyl-D-aspartate receptor antagonist having analgesic activity or utility.

As used herein, a "COXi" is a cyclooxygenase inhibitor, such as Ketorolac, Acetaminophen, Parecoxib, Ibuprofen, Meloxicam, Diclofenac, Ketoprofen, Celecoxib, Naproxen Sodium, Tolmetin, Etodolac, Fenoprofen, Indomethacin, Carprofen, Diflunisal, Nabumetone, Dexketoprofen, or any other parenteral drug in this class.

As defined herein, a unit of concentration represented as "1:100,000" is equivalent to 1 mg in 1 ml (or 1000 μg in 1 ml). For example, a concentration of 1% is equal to 10 mg/cc (or 10 mg/ml), 0.5% is equal to 5 mg per cc, 0.25% is equal to 2.5 mg per cc, 0.10% is equal to 1.0 mg per cc and so forth.

As used herein, postoperative nausea and vomiting (PONV) is defined as any nausea, retching, or vomiting occurring during the first 24-48 h after surgery in surgical patients.

DETAILED DESCRIPTION OF THE INVENTION

The present invention discloses opioid-free analgesic, anesthetic, anti-nociceptive, antalgic, anti-inflammatory formulations, e.g., multimodal opioid-sparing analgesia (MMOSA) formulations. The MMOSA formulations herein are clinically and extraordinarily effective to significantly reduce or eliminate postoperative nausea and vomiting and significantly enhance postoperative pain relief and avoid or eliminate opioid related adverse drug effects as compared to existing prior art anesthetics/analgesics. The formulations of the present invention comprise a synergistic and multimodal admixture of drugs. Without wishing to limit the present invention to any theory or mechanism, it is believed that the drugs in the formulations of the present invention work together in multimodal added synergism to prevent nociception and the perception of pain while decreasing nausea and vomiting, reducing or eliminating opioid exposure and opioid related adverse drug effects effectively and preemptively. The combination of the drugs provides for prolonged and effective analgesia with minimal toxicity, greater ease of use, and reduced side effects including anti-emesis. The invention is a multimodal opioid-free anti-emetic innovative admixture. The invention is multimodal with the individual components also demonstrating independent synergistic multimodal analgesic mechanisms of action. The invention provides an unexpected and surprising clinically significant, unanticipated, antiemetic benefit.

The present invention also includes methods featuring administration of the MMOSA formulations for treating and/or managing, and/or preemptively preventing pain, and/or reducing pain, and/or significantly decreasing postoperative nausea and vomiting. For example, the present invention features methods of treating pain, managing pain, reducing pain, preventing pain, reducing exposure to opioids and adverse effects, reducing nausea and vomiting, in a subject in need of such treatment. The methods comprise administering an effective amount of a formulation according to the present invention, a MMOSA formulation, as described herein, to a subject (e.g., a mammal) in need of such treatment.

MMOSA Formulations Comprising a Local Anesthetic, a NMDA Receptor Antagonist, and a COX Inhibitor As previously discussed, the present invention discloses opioid-free analgesic, anesthetic, anti-nociceptive, analgesic, anti-inflammatory formulations, exemplar multimodal opioid-sparing analgesia (MMOSA) formulations. The MMOSA formulations herein are clinically and extraordinarily effective to significantly reduce postoperative nausea and vomiting and significantly enhance postoperative pain relief and avoid opioid exposure as compared to existing prior art anesthetics/analgesics.

As a non-limiting example, the multimodal, synergistic formulation (MMOSA formulation) may comprise an amide local anesthetic at about 0.01%-0.5%, an N-methyl-D-aspartate (NMDA) receptor antagonist at about 0.01-3.0 mg/cc, and a cyclooxygenase (COX) inhibitor at about 0.01-1.5 mg/cc. In some embodiments, the formulation comprises Bupivacaine Hydrochloride, Ketamine Hydrochloride, and Ketorolac Tromethamine (referred to as "BKK"). In some embodiments, the formulation comprises Bupivacaine Hydrochloride, Ketamine Hydrochloride, and Ketorolac Tromethamine at a concentration of 0.01% to 0.5%, 0.01 to 3 mg/ml, and 0.01 to 1.5 mg/ml, respectively. The present invention is not limited to BKK, nor the aforementioned concentrations.

In some embodiments, the local anesthetic comprises Bupivacaine Hydrochloride, Ropivacaine Hydrochloride, or Levobupivacaine Hydrochloride. In some embodiments, the local anesthetic comprises Lidocaine, Prilocaine, Amethocaine, Procaine, Cinchocaine, Mepivacaine, Etidocaine, Tetracaine or any other long or short acting local anesthetic, including ester type local anesthetics and amide type local anesthetics.

In some embodiments, the NMDA receptor antagonist comprises Ketamine (Ketamine Hydrochloride), Trolamine, Tramadol, Dextromethorphan, Meperidine, Minocycline, Agmatine, Magnesium Sulfate, Aptiganel, or any other analgesic or anesthetic phencyclidine derivative having NMDA receptor antagonist activity.

In some embodiments, the COX inhibitor comprises Ketorolac (Ketorolac Tromethamine), Acetaminophen, Parecoxib, Ibuprofen, Meloxicam, Diclofenac, Ketoprofen, Celecoxib, Dexketoprofen, Carprofen, or any other parental drug in this class.

In some embodiments, the concentration of Bupivacaine Hydrochloride, Ropivacaine Hydrochloride, or Levobupivacaine Hydrochloride is about 0.125%. In some embodiments, the concentration of Bupivacaine Hydrochloride, Ropivacaine Hydrochloride, or Levobupivacaine Hydrochloride is between about 0.01% to 0.05%. In some embodiments, the concentration of Bupivacaine Hydrochloride, Ropivacaine Hydrochloride, or Levobupivacaine Hydrochloride is between about 0.025% to 0.075%. In some embodiments, the concentration of Bupivacaine Hydrochloride, Ropivacaine Hydrochloride, or Levobupivacaine Hydrochloride is between about 0.05% to 0.1%. In some embodiments, the concentration of Bupivacaine Hydrochloride, Ropivacaine Hydrochloride, or Levobupivacaine Hydrochloride is between about 0.05% to 0.125%. In some embodiments, the concentration of Bupivacaine Hydrochloride, Ropivacaine Hydrochloride, or Levobupivacaine Hydrochloride is between about 0.1% to 0.15%. In some embodiments, the concentration of Bupivacaine Hydrochloride, Ropivacaine Hydrochloride, or Levobupivacaine Hydrochloride is between about 0.1% to 0.2%. In some embodiments, the concentration of Bupivacaine Hydrochloride, Ropivacaine Hydrochloride, or Levobupivacaine Hydrochloride is between about 0.125% to 0.2%. In some embodiments, the concentration of Bupivacaine Hydrochloride, Ropivacaine Hydrochloride, or Levobupivacaine Hydrochloride is between about 0.15% to 0.25%. In some embodiments, the concentration of Bupivacaine Hydrochloride, Ropivacaine Hydrochloride, or Levobupivacaine Hydrochloride is between about 0.2% to 0.3%. In some embodiments, the concentration of Bupivacaine Hydrochloride, Ropivacaine Hydrochloride, or Levobupivacaine Hydrochloride is between about 0.3% to 0.4%. In some embodiments, the concentration of Bupivacaine Hydrochloride, Ropivacaine Hydrochloride, or Levobupivacaine Hydrochloride is between about 0.4% to 0.5%. In some embodiments, the concentration of Bupivacaine Hydrochloride, Ropivacaine Hydrochloride, or Levobupivacaine Hydrochloride is between about 0.5% to 0.6%. In some embodiments, the concentration of Bupivacaine Hydrochloride, Ropivacaine Hydrochloride, or Levobupivacaine Hydrochloride is between about 0.6% to 0.7%. In some embodiments, the concentration of Bupivacaine Hydrochloride, Ropivacaine Hydrochloride, or Levobupivacaine Hydrochloride is between about 0.5% to 0.75%. In some embodiments, the concentration of Bupivacaine Hydrochloride, Ropivacaine Hydrochloride, or Levobupivacaine Hydrochloride is more than about 0.75%. A student of the amide local anesthetic art will realize the current useful amide local anesthetics in clinically efficacious concentrations would be interchangeable in an exemplary analgesic admixture.

In some embodiments, the concentration of Ketamine Hydrochloride is about 1 mg/ml. In some embodiments, the concentration of Ketamine Hydrochloride is between about 0.1 to 0.5 mg/ml. In some embodiments, the concentration of Ketamine Hydrochloride is between about 0.5 to 1.0 mg/ml. In some embodiments, the concentration of Ketamine Hydrochloride is between about 0.5 to 1.5 mg/ml. In some embodiments, the concentration of Ketamine Hydrochloride is between about 1 to 2 mg/ml. In some embodiments, the concentration of Ketamine Hydrochloride is between about 1 to 3 mg/ml. In some embodiments, the concentration of Ketamine Hydrochloride is more than 3 mg/ml and may exceed 10 mg/ml. A student of the NMDA receptor antagonist art will realize the interchangeable drug in the same class at clinically useful dosages would enhance the non-opioid actions of an exemplary opioid free multimodal analgesic and anti-emetic admixture. In some embodiments, the Ketamine (Ketamine Hydrochloride) is a racemic admixture. In some embodiments, the Ketamine (Ketamine Hydrochloride) is the R- or S-enantiomer. In some embodiments the concentration of another substituted NMDA receptor antagonist will be similar to, or equipotent to, the Ketamine (Ketamine Hydrochloride) concentration or any other NMDA receptor antagonist of a clinically effective substituted concentration providing effective analgesia, antinociception, anti-inflammatory, and analgesic pharmacologic effects.

In some embodiments, the concentration of Ketorolac (Ketorolac Tromethamine) is about 0.2 mg/ml. In some embodiments, the concentration of Ketorolac Tromethamine is between about 0.01 to 1.0 mg/ml. In some embodiments, the concentration of Ketorolac Tromethamine is between about 0.05 to 0.95 mg/ml. In some embodiments, the concentration of Ketorolac Tromethamine is between about 0.15 to 0.95 mg/ml. In some embodiments, the concentration of Ketorolac Tromethamine is between about 0.1 to 0.2 mg/ml. In some embodiments, the concentration of Ketorolac Tromethamine is between about 0.2 to 0.3 mg/ml. In some embodiments, the concentration of Ketorolac Tromethamine is about 0.3 to 1.0 mg/ml. In some embodiments, the concentration of Ketorolac Tromethamine is about 1.0 to 1.5 mg/ml. In some embodiments the concentration of Ketorolac Tromethamine is greater than 1.5 mg/ml. In some embodiments, the Ketorolac Tromethamine is a racemic admixture. In some embodiments, the Ketorolac Tromethamine is the R- or S-enantiomer. In some embodiments, the concentration of Parecoxib, Diclofenac, Ibuprofen, Meloxicam, Ketoprofen, Dexketoprofen, Carprofen or any other parenteral cyclooxygenase inhibitor is similar to, or equipotent to, the clinically effective Ketorolac (Ketorolac Tromethamine) concentration or any other COX inhibitor of a clinically effective substituted concentration providing effective analgesia, antinociception, anti-inflammatory, and analgesic pharmacologic effects. A student of the parenteral cyclooxygenase art will understand the interchange or addition of a COX inhibitor other than Ketorolac (Ketorolac Tromethamine) would provide a similar analgesic effect when combined with the other classes of analgesics in the exemplary multimodal opioid free analgesic formulation.

In some embodiments, the formulation further comprises an alpha agonist, a second alpha-2-central agonist (alpha agonist), a steroid, a transient receptor potential vanilloid (TRPV) receptor antagonist or agonist, an antibiotic, a protein kinase inhibitor, a competitive or non-competitive glycine or glutamate antagonist, glutamate or glycine inhibitor, a cyclooxygenase 3 inhibitor (Acetaminophen), an anti-fibrinolytic, or combinations thereof.

Some aspects of the invention comprise at least a local anesthetic comprising Bupivacaine (Bupivacaine Hydrochloride), a NMDA receptor antagonist, and a COX inhibitor. In some aspects in which the local anesthetic comprises Bupivacaine Hydrochloride, the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac (Ketorolac Tromethamine); the NMDA receptor antagonist comprises Tramadol, and the COX inhibitor comprises Ketorolac (Ketorolac Tromethamine); the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac;

the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Lidocaine, an NMDA receptor antagonist, and a COX inhibitor. In some aspects the local anesthetic comprises Lidocaine and; the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Ropivacaine (Ropivacaine Hydrochloride), an NMDA receptor antagonist, and a COX inhibitor. In some aspects: the local anesthetic comprises Ropivacaine Hydrochloride and: the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Artisanal, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Levobupivacaine (Levobupivacaine Hydrochloride), an NMDA receptor antagonist, and a COX inhibitor. In some aspects, the local anesthetic comprises Levobupivacaine Hydrochloride and: the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxic; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Prilocaine, an NMDA receptor antagonist, and a COX inhibitor. In some aspects, the local anesthetic comprises Prilocaine and: the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Amethocaine, an NMDA receptor antagonist, and a COX inhibitor. In some embodiments, the local anesthetic comprises Amethocaine and: the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Procaine, an NMDA receptor antagonist, and a COX inhibitor. In some aspects, the local anesthetic comprises Procaine and: the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Cinchocaine, an NMDA receptor antagonist, and a COX inhibitor. In some aspects, the local anesthetic comprises Cinchocaine and: the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Mepivacaine, an NMDA receptor antagonist, and a COX inhibitor. In some aspects, the local anesthetic comprises Mepivacaine and: the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Etidocaine, an NMDA receptor antagonist, and a COX inhibitor. In some aspects, the local anesthetic comprises Etidocaine and: the NMDA receptor antagonist comprises Ketamine Hydrochloride, and the COX inhibitor comprises Ketorolac Tromethamine; the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

Some aspects of the invention comprise at least a local anesthetic comprising Tetracaine, an NMDA receptor antagonist, and a COX inhibitor. In some aspects, the local anesthetic comprises Tetracaine and: the NMDA receptor antagonist comprises Trolamine, and the COX inhibitor comprises Ketorolac Tromethamine; the NMDA receptor antagonist comprises Tramadol, and the COX inhibitor comprises Ketorolac Tromethamine; the NMDA receptor antagonist comprises Dextromethorphan, and the COX inhibitor comprises Ketorolac Tromethamine; the NMDA receptor antagonist comprises Meperidine, and the COX inhibitor comprises Ketorolac Tromethamine; the NMDA receptor antagonist comprises Minocycline, and the COX inhibitor comprises Ketorolac Tromethamine; the NMDA receptor antagonist comprises Agmatine, and the COX inhibitor comprises Ketorolac Tromethamine; the NMDA receptor antagonist comprises Magnesium Sulfate, and the COX inhibitor comprises Ketorolac Tromethamine; the NMDA receptor antagonist comprises Aptiganel, and the COX inhibitor comprises Ketorolac Tromethamine; the NMDA receptor antagonist comprises Ketamine Hydrochloride, and the COX inhibitor comprises Acetaminophen; the NMDA receptor antagonist comprises Trolamine, and the COX inhibitor comprises Acetaminophen; the NMDA receptor antagonist comprises Tramadol, and the COX inhibitor comprises Acetaminophen; the NMDA receptor antagonist comprises Dextromethorphan, and the COX inhibitor comprises Acetaminophen; the NMDA receptor antagonist comprises Meperidine, and the COX inhibitor comprises Acetaminophen; the NMDA receptor antagonist comprises Minocycline, and the COX inhibitor comprises Acetaminophen; the NMDA receptor antagonist comprises Agmatine, and the COX inhibitor comprises Acetaminophen; the NMDA receptor antagonist comprises Magnesium Sulfate, and the COX inhibitor comprises Acetaminophen; the NMDA receptor antagonist comprises Aptiganel, and the COX inhibitor comprises Acetaminophen; the NMDA receptor antagonist comprises Ketamine Hydrochloride, and the COX inhibitor comprises Parecoxib; the NMDA receptor antagonist comprises Trolamine, and the COX inhibitor comprises Parecoxib; the NMDA receptor antagonist comprises Tramadol, and the COX inhibitor comprises Parecoxib; the NMDA receptor antagonist comprises Dextromethorphan, and the COX inhibitor comprises Parecoxib; the NMDA receptor antagonist comprises Meperidine, and the COX inhibitor comprises Parecoxib; the NMDA receptor antagonist comprises Minocycline, and the COX inhibitor comprises Parecoxib; the NMDA receptor antagonist comprises Agmatine, and the COX inhibitor comprises Parecoxib; the NMDA receptor antagonist comprises Magnesium Sulfate, and the COX inhibitor comprises Parecoxib; the NMDA receptor antagonist comprises Aptiganel, and the COX inhibitor comprises Parecoxib; the NMDA receptor antagonist comprises Ketamine Hydrochloride, and the COX inhibitor comprises Ibuprofen; the NMDA receptor antagonist comprises Trolamine, and the COX inhibitor comprises Ibuprofen; the NMDA receptor antagonist comprises Tramadol, and the COX inhibitor comprises Ibuprofen; the NMDA receptor antagonist comprises Dextromethorphan, and the COX inhibitor comprises Ibuprofen; the NMDA receptor antagonist comprises Meperidine, and the COX inhibitor comprises Ibuprofen; the NMDA receptor antagonist comprises Minocycline, and the COX inhibitor comprises Ibuprofen; the NMDA receptor antagonist comprises Agmatine, and the COX inhibitor comprises Ibuprofen; the NMDA receptor antagonist comprises Magnesium Sulfate, and the COX inhibitor comprises Ibuprofen; the NMDA receptor antagonist comprises Aptiganel, and the COX inhibitor comprises Ibuprofen; the NMDA receptor antagonist comprises Ketamine Hydrochloride, and the COX inhibitor comprises Meloxicam; the NMDA receptor antagonist comprises Trolamine, and the COX inhibitor comprises Meloxicam; the NMDA receptor antagonist comprises Tramadol, and the COX inhibitor comprises Meloxicam; the NMDA receptor antagonist comprises Dextromethorphan, and the COX inhibitor comprises Meloxicam; the NMDA receptor antagonist comprises Meperidine, and the COX inhibitor comprises Meloxicam; the NMDA receptor antagonist comprises Minocycline, and the COX inhibitor comprises Meloxicam; the NMDA receptor antagonist comprises Agmatine, and the COX inhibitor comprises Meloxicam; the NMDA receptor antagonist comprises Magnesium Sulfate, and the COX inhibitor comprises Meloxicam; the NMDA receptor antagonist comprises Aptiganel, and the COX inhibitor comprises Meloxicam; the NMDA receptor antagonist comprises Ketamine Hydrochloride, and the COX inhibitor comprises Diclofenac; the NMDA receptor antagonist comprises Trolamine, and the COX inhibitor comprises Diclofenac; the NMDA receptor antagonist comprises Tramadol, and the COX inhibitor comprises Diclofenac; the NMDA receptor antagonist comprises Dextromethorphan, and the COX inhibitor comprises Diclofenac; the NMDA receptor antagonist comprises Meperidine, and the COX inhibitor comprises Diclofenac; the NMDA receptor antagonist comprises Minocycline, and the COX inhibitor comprises Diclofenac; the NMDA receptor antagonist comprises Agmatine, and the COX inhibitor comprises Diclofenac; the NMDA receptor antagonist comprises Magnesium Sulfate, and the COX inhibitor comprises Diclofenac; the NMDA receptor antagonist comprises Aptiganel, and the COX inhibitor comprises Diclofenac; the NMDA receptor antagonist comprises Ketamine Hydrochloride, and the COX inhibitor comprises Ketoprofen or Dexketoprofen; the NMDA receptor antagonist comprises Trolamine, and the COX inhibitor comprises Ketoprofen or Dexketoprofen; the NMDA receptor antagonist comprises Tramadol, and the COX inhibitor comprises Ketoprofen; the NMDA receptor antagonist comprises Dextromethorphan, and the COX inhibitor comprises Ketoprofen or Dexketoprofen; the NMDA receptor antagonist comprises Meperidine, and the COX inhibitor comprises Ketoprofen or Dexketoprofen; the NMDA receptor antagonist comprises Minocycline, and the COX inhibitor comprises Ketoprofen or Dexketoprofen; the NMDA receptor antagonist comprises Agmatine, and the COX inhibitor comprises Ketoprofen or Dexketoprofen; the NMDA receptor antagonist comprises Magnesium Sulfate, and the COX inhibitor comprises Ketoprofen or Dexketoprofen; the NMDA receptor antagonist comprises Aptiganel, and the COX inhibitor comprises Ketoprofen or Dexketoprofen; the NMDA receptor antagonist comprises Ketamine Hydrochloride, and the COX inhibitor comprises Celecoxib; the NMDA receptor antagonist comprises Trolamine, and the COX inhibitor comprises Celecoxib; the NMDA receptor antagonist comprises Tramadol, and the COX inhibitor comprises Celecoxib; the NMDA receptor antagonist comprises Dextromethorphan, and the COX inhibitor comprises Celecoxib; the NMDA receptor antagonist comprises Meperidine, and the COX inhibitor comprises Celecoxib; the NMDA receptor antagonist comprises Minocycline, and the COX inhibitor comprises Celecoxib; the NMDA receptor antagonist comprises Agmatine, and the COX inhibitor comprises Celecoxib; the NMDA receptor antagonist comprises Magnesium Sulfate, and the COX inhibitor comprises Celecoxib; the NMDA receptor antagonist comprises Aptiganel, and the COX inhibitor comprises Celecoxib; the NMDA receptor antagonist comprises Ketamine Hydrochloride, and the COX inhibitor comprises Carprofen; the NMDA receptor antagonist comprises Trolamine, and the COX inhibitor comprises Carprofen; the NMDA receptor antagonist comprises Tramadol, and the COX inhibitor comprises Carprofen; the NMDA receptor antagonist comprises Dextromethorphan, and the COX inhibitor comprises Carprofen; the NMDA receptor antagonist comprises Meperidine, and the COX inhibitor comprises Carprofen; the NMDA receptor antagonist comprises Minocycline, and the COX inhibitor comprises Carprofen; the NMDA receptor antagonist comprises Agmatine, and the COX inhibitor comprises Carprofen; the NMDA receptor antagonist comprises Magnesium Sulfate, and the COX inhibitor comprises Carprofen; or the NMDA receptor antagonist comprises Aptiganel, and the COX inhibitor comprises Carprofen.

In some embodiments, the formulation further comprises a Transient Potential Vanilloid (TRPV) Receptor agonist or antagonist. In some embodiments, the TRVP agonist is Capsaicin or Resiniferatoxin, or any other agonist. In some embodiments, the TRVP antagonist is Capazepine or any other aryl urea cinnamide, or carboxamide antagonist. In some embodiments, the TRPV receptor agonist or antagonist is in a dose of 400 micrograms to 10,000 micrograms in 20 to 120 cc of an acceptable vehicle (e.g., 3-200 micrograms/cc). The present invention is not limited to the aforementioned concentrations.

In some embodiments, the formulation further comprises a protein kinase inhibitor. In some embodiments, the protein kinase inhibitor is Temsirolimus. In some embodiments, the protein kinase inhibitor is at a concentration of 0.001 mg/cc to 0.1 mg/cc. The present invention is not limited to the aforementioned concentrations.

In some embodiments, the formulation further comprises a competitive or non-competitive glycine or glutamate antagonist. Non-limiting examples of the competitive or non-competitive glycine or glutamate antagonist are Magnesium Sulfate, Remacemide, and Tiletamine. In some embodiments, the concentration of the competitive or non-competitive glycine or glutamate antagonist is 0.001 mg/cc to 0.1 mg/cc. The present invention is not limited to the aforementioned concentrations.

In some embodiments, the formulation further comprises Acetaminophen or Paracetamol, or other parental cyclooxygenase type 3 inhibitors, e.g., at doses of 1 mg/cc to 20 mg/cc. The present invention is not limited to the aforementioned concentrations.

In some embodiments, the formulation comprises an alpha agonist, e.g., an alpha 2 agonist. Non-limiting examples of alpha 2 agonists include, but are not limited to, Clonidine, Dexmedetomidine, Tizanidine, Phenylephrine, Meperidine, Methadone, Tramadol, Guanfacine, and Medetomidine. In some embodiments, the concentration of the alpha agonist, which in some embodiments may be an alpha 2 agonist, is 0.02 mg/cc to 0.1 mg/cc. For example, the concentration of Clonidine or Dexmedetomidine may be from 0.02 mg/cc to 0.1 mg/cc. In some embodiments, the concentration of the alpha agonist may be from 2.5 micrograms/cc to 40 micrograms/cc. In some embodiments, the concentration of the alpha agonist may be from 1 micrograms/cc to 60 micrograms/cc. In some embodiments, the concentration of the alpha agonist may be from 1 micrograms/cc to 100 micrograms/cc. In some embodiments, the concentration of the alpha agonist may be from 0.1 micrograms/cc to 100 micrograms/cc.

As a non-limiting example, in some embodiments, the formulation comprises Ropivacaine, Epinephrine, Clonidine, and Ketorolac. In some embodiments, the concentration of Ropivacaine is from 2-3 mg/cc, e.g., about 2.46 mg/cc. In some embodiments, the concentration of Epinephrine is about 0.005 mg/cc. In some embodiments, the concentration of Clonidine is about 0.0008 mg/cc. In some embodiments, the concentration of Ketorolac is about 0.3 mg/cc.

As a non-limiting example, in some embodiments, the formulation comprises Ropivacaine, Epinephrine, Dexmedetomidine, and Ketorolac. In some embodiments, the concentration of Ropivacaine is from 2-3 mg/cc, e.g., about 2.46 mg/cc. In some embodiments, the concentration of Epinephrine is about 0.005 mg/cc. In some embodiments, the concentration of Dexmedetomidine is about 0.0008 mg/cc. In some embodiments, the concentration of Ketorolac is about 0.3 mg/cc.

In some embodiments the formulation contains a steroid. Non-limiting examples of steroids include but are not limited to Dexamethasone, Methylprednisolone, Betamethasone Propionate, Betamethasone Sodium Phosphate, Diprospan (Betamethasone disodium phosphate and Betamethasone dipropionate), or another anti-inflammatory mineral corticosteroid or glucocorticosteroid. In some embodiments, the steroid is at a concentration of 0.01 mg/cc to 1 mg/cc. The present invention is not limited to the aforementioned concentrations.

In some embodiments, the MMOSA formulation further comprises the alpha agonist Epinephrine. In some embodiments, a concentration of Epinephrine is between about 1:200,000 to 1:800,000.

In some embodiments, the MMOSA formulation further contains and comprises an antibiotic. Non-limiting examples of antibiotics include beta-lactam antibiotics. Non-limiting examples of antibiotics include Cephalexin, Cefazolin, Cefaclor, Cefuroxime, Ceftibuten, Penicillin V, Nafcillin, Amoxicillin, Ampicillin, or any of the other cephalosporins for penicillinase resistant antibiotics in the class, including beta-lactam inhibitors. In some embodiments, the concentration of the antibiotic is from 1-20 mg/cc. In some embodiments, the MMOSA formulation further contains Vancomycin. In some embodiments, the MMOSA formulation contains an antifibrinolytic, e.g., Tranexamic Acid, Epsilon-aminocaproic acid, or other lysine analogs, Aprotinin, or any other serine protease inhibitor, or any other drug or compound in this class. In some embodiments the concentration of Tranexamic Acid is 5 to 20 mg/cc.

In some embodiments, the formulations herein, e.g., the multi-modal opioid sparing analgesia (MMOSA) formulations, further comprise a saline solution. As an example, in some embodiments, Bupivacaine Hydrochloride is added to the saline solution at a desired concentration. In some embodiments, Ketorolac Tromethamine and Ketamine Hydrochloride is added to the Bupivacaine Hydrochloride and saline solution. The Examples section below describes non-limiting examples of preparation of MMOSA formulations.

In some embodiments, the MMOSA formulation has an increased shelf life as compared to the shelf lives of the individual components of the formulation. In some embodiments, the MMOSA formulation comprises a buffer for enhancing shelf life. In some embodiments, the active pharmaceutical ingredients are lyophilized. In some embodiments, the formulation comprises a buffer for raising or lowering the pKa of the formulation. Buffers are used to control a pH of a formulation by preventing pronounced variations in pH during use or storage. Preferably, the buffers may buffer the formulation from a pH of about 7.3 to a pH of about 7.6, more preferably from a pH of about 7.35 to a pH of about 7.5, and most preferably from a pH of about 7.3 to a pH of about 7.4. Non-limiting examples of buffers include citric acid, triethanolamine, acetates, and phosphates. By inhibiting inflammation at the infiltration site, the anti-inflammatory actions of the MMOSA components, e.g., specifically the addition of a COXi, may favorably improve the pharmacokinetics of the MMOSA at the site of surgical inflammation adding to improved efficacy of the amide local anesthetic component, increasing the unionized to ionized ratio of the local anesthetic at the targeted site of action improving efficacy of the sodium channel transduction blockade of nociceptive signaling.

Without wishing to limit the present invention to any theory or mechanism, it is believed that the MMOSA formulation of the present invention has a bactericidal and/or a bacteriostatic effect.

In some embodiments, the MMOSA formulation of the present invention is used as a preemptive analgesic. Preemptive analgesics are administered prior to the onset of nociceptive stimuli as a means to prevent, reduce, or modulate nociceptive transduction, transmission, sensitization and ensuing pain perception.

In some embodiments, the formulations further comprise a neurokinin-1 (NK-1) receptor antagonist. Likewise, the present invention also features a method for treating post-surgical pain in a patient in need thereof comprising administering to the patient a therapeutically effective amount of a neurokinin-1 (NK-1) receptor antagonist in combination with a MMOSA formulation. In some clinical uses, embodiments, the post-surgical pain to be treated is not neuropathic pain. In preferred embodiments, the NK-1 receptor antagonist is selected from a group consisting of Aprepitant, Rolapitant, Netupitant, Lanepitant, Vestipitant, Orvepitant Maleate, Casopitant, Ezlopitant, Serlopitant, Grapiprant, Fosaprepitant, Befetupitant, Maropitant, or a pharmaceutically acceptable salt thereof. For example, the NK-1 receptor antagonist may be Fosaprepitant. Dose ranges of the NK-1 receptor antagonist may range from 0.1 mg/kg to 5 mg/kg. In other embodiments, two or more neurokinin-1 (NK-1) receptor antagonists may be combined and administered to the patient. For example, Fosapreitant may optionally be combined with Vestipitant and Casopitant. Fasoaprepitant may be included in the formulation in a dosage range of about 30 mg to about 150 mg. When Vestipitant is included in the formulation, it may be provided in a dosage range of about 0.001 mg to about 200 mg. Alternatively or in conjunction, when Casopitant is included in the formulation, it may be provided in a dosage range of about 15 mg to about 150 mg.

In preferred embodiments, the pain medication used in combination with the NK-1 receptor antagonist may be selected from local anesthetics, opioids, non-steroid anti-inflammatory drugs (NSAID), anticonvulsants, NMDA antagonists, serotonin and norepinephrine reuptake inhibitors (SNRIs), Acetaminophen, and tricyclic antidepressants.

Surprising Effects

Surprisingly and unexpectedly, more than 92% of patients treated with BKK (one example of the MMOSA formulations herein) infiltrative formulation for Lumbar Discectomies, Decompressive Lumbar Laminectomies, Anterior Cervical Discectomies and Peripheral Nerve Decompressive Procedure surgeries reported very statistically and clinically significant, surprising, and unexpected low to no PONV after 24 hours postoperatively. Importantly, 100% of patients treated with existing unimodal opioid analgesics for the same surgeries would be predicted to report significant PONV after 24 hours of being treated with prior art anesthetics/analgesics. Notably, a majority of patients treated with prior art analgesic techniques, for the same surgeries, would predictably still suffer noticeable PONV after 48 hours of being administered prior art analgesics, almost uniformly opioids.

In one embodiment, 84.8% of patients of the population of patients (>4000 consecutive) treated with BKK (one example of the MMOSA formulations herein) reported no to mild pain, 13.5% reported moderate pain, with only 1.6% of the population of treated patients reporting severe pain through 24 hours postoperatively.

As used herein, the term "infiltrative analgesia" describes analgesia, anti-nociception, anti-inflammatory effects produced in a local nociceptive field by injecting the analgesic agent into and around operative sites, wounds, incisions, or adjacent fascial planes. Examples of fascial plane blocks include but are not limited to transverse abdominis plane, brachial or lumbar plexus plane, erector spinae plane, sympathetic plane or ganglion blocks, or peripheral nerve blocks.

As for an example, Shaikh S, et al. reported that in lumbar surgery, like Lumbar Microdiscectomy, where the anesthetics and analgesics administered intravenously intraoperatively were Propofol 2-2.5 mg·kg-1, Midazolam 1-2 mg, and Fentanyl 1-1.5 µg·kg-1 followed by intravenous Morphine or Ketorolac (Ketorolac Tromethamine). Here, Shaikh S. reported an incidence of postoperative nausea of 61% and postoperative vomiting of 9.4%. Most notably, 16% of patients in Shaikh's series suffered severe postoperative nausea and vomiting with a resultant hospital readmission rate of 5.7% due to severe PONV, whereas only 0.18% patients through 24 hours reported severe PONV in BKK formulation treatment in similar lumbar surgeries with no reported hospital admission or readmission (Table 1 below). Cruthirds D. et al.[5] also demonstrated that after outpatient surgery, the overall incidence of post discharge nausea has been reported to be 17% and of vomiting 8% which was not seen in over 4000 consecutive patients treated with the BKK Formulation through 24 hours postoperatively.

Recently, Patel prior art demonstrated that Ketamine mixed with Bupivacaine as an intrathecal injectable provided better analgesia than Bupivacaine alone. However, the prior art Patel publication cannot be considered as a guideline or teaching to combine Bupivacaine and Ketamine to reduce PONV because Patel further reported that in the 50 patients studied by her, 28% developed PONV in the intrathecal Bupivacaine only group, and 36% developed PONV in the intrathecal Bupivacaine plus Ketamine group. This PONV incidence of Patel as compared to the reported 4000 consecutive neurosurgical cases using Bupivacaine Hydrochloride as the local anesthetic, Ketamine Hydrochloride as the NMDA receptor antagonist, and Ketorolac Tromethamine as the COX inhibitor used in an infiltrative block, where surprisingly and unexpectedly, 92.7% of all patients through 24 hours postoperatively reporting no PONV (Table 1 below). Patel, et al. does not teach or suggest adding the COX inhibitor, Ketorolac Tromethamine in the intrathecal anesthetic/analgesic composition. Patel also reported from other literature that the administration of Ketamine, alone or in combination with other analgesics, is associated with an increased incidence of PONV and other postoperative complications. Clearly and importantly, the Patel prior art clearly does not motivate or teach, and in fact, teaches, it is counterintuitive, to combine Ketamine with Bupivacaine in order to reduce the incidence of PONV at the time the present invention was discovered. Here, the Patel prior art implicitly teaches away, or in other words, Patel et al. guided attentive clinicians in an opposite directive from the indication, whereas the present invention proceeded and originated contrary to this prior art. Table 1 summarizes this discussion and the unexpected, surprising, and contrary results using innovative MMOSA.

TABLE 1

| | PONV (nausea & vomiting for the first 24-48 hours post-surgery) | | | |
|---|---|---|---|---|
| Formulation | % of patients with NO PONV | % of patients with SEVERE PONV | Reference | Conclusion |
| BKK MMOSA | >92% | 0.18% | Present Invention | Dramatic and superior reduction in PONV for BKK |

TABLE 1-continued

PONV (nausea & vomiting for the first 24-48 hours post-surgery)

| Formulation | % of patients with NO PONV | % of patients with SEVERE PONV | Reference | Conclusion |
| --- | --- | --- | --- | --- |
| Propofol, Midazolam, and Fentanyl at induction followed by intravenous Morphine or Ketorolac Tromethamine as additional analgesia | 30% | 16% | Shaikh et al. | Higher incidence of PONV |
| Bupivacaine Hydrochloride + Saline | 72% | No data | Patel et al. | Presence of Ketamine increases PONV. In contrast, BKK surprisingly reduced PONV. |
| Bupivacaine Hydrochloride + Ketamine Hydrochloride | 64% | No data | | |

Clearly, one of ordinary skill would not be able to make a projection or prediction from Patel that the combination of Bupivacaine (Bupivacaine Hydrochloride), Ketamine (Ketamine Hydrochloride), and Ketorolac (Ketorolac Tromethamine) would result in an anesthetic/analgesic that provides a clinically important and statistically significant reduction in postoperative PONV, in which surprisingly and unexpectedly, 92.7% of over 4000 consecutive patients reported no PONV, 0% reported mild PONV, 5.37% reported moderate PONV, and 0.18% reported severe PONV through 24 hours post operatively.

It is well documented in the literature that postoperative pain can have a significant impact on patient recovery, patient safety and experience. Apfelbaum, J. et al. reported of the approximately 73,000,000 surgeries performed in the United States each year, 80% of those patients experience postoperative pain from the immediate postoperative period until 2 weeks after discharge. Of those patients studied by Apfelbaum, 86% reported moderate, severe, or extreme pain and 25% of those patients who received standard of care unimodal opioid-based analgesia reported an opioid adverse drug effect, the majority of times PONV. Gan T. J, et al[10] interviewed 300 patients having surgery within the previous five years finding, 86% experienced pain after surgery, and of these, 75% reported moderate to extreme pain immediately post-operation, with 74% experiencing pain after discharge. Therefore, there is an urgent, and prior to, the present invention, an unmet clinical need to develop, invent, an improved exemplary opioid free multimodal analgesic formulation to significantly reduce postoperative pain and postoperative nausea and vomiting for patients undergoing painful surgeries or painful procedures.

The opioid-free formulation of the present invention allows for a non-addictive simple and effective alternative to pain management without the morbidity of PONV. This approach is especially critical to help prevent opioid addiction and overdose that may result from using opioids for the tens of millions of inpatient and outpatient procedures performed annually in the US and contributing to the current opioid crisis. As of October 2017, the US Government declared the opioid crisis pandemic, a public health emergency. Opioid overdoses claimed over 100,000 lives in 2022, with 45-50 overdose deaths per day. In the US, a patient dies of an opioid overdose every 4-10 minutes. There are over 53 million inpatient and 57 million outpatient procedures performed in the US annually and the majority are exposed to opioids. Of patients treated with opioids perioperatively and prescribed opioids postoperatively, one patient of every 7 treated with opioids will have morbidity, and of these patients an increased risk of mortality.

The Joint Council of Economic Advisors found that the cost of the current Opioid Pandemic in 2020 to be more than 1.5 trillion dollars annually, up 37% from 2017 when measured and reported by the CDC. Therefore, the current invention provides an opioid-free analgesic/anesthetic allowing for a "non-addictive", much needed innovation, to treat acute pain and avoid or eliminate an initial or repeated opioid exposure, opioid related adverse effects, morbidity, and mortality.

According to some embodiments, surprisingly, more than 25% of postoperative neurosurgical patients treated with an intraoperative MMOSA formulation (BKK infiltrative formulation) for Lumbar Discectomies, Decompressive Lumbar Laminectomies, Anterior Cervical Discectomies with Fusion and Peripheral Nerve Decompressive surgeries reported NO PAIN through 24 hours in 4000 consecutive neurosurgical cases. Among these same 4000 consecutive neurosurgical cases, through 24 hours postoperatively, 25.40% reported no pain, 59.4% patients reported mild pain, 13.5% patients reported moderate pain, and only 1.6% reported severe pain. The discovery that opioid-free multimodal opioid sparing BKK is an effective, exemplary, multimodal anesthetic/analgesic that abolishes pain completely in more than 25% of 4000 consecutive painful neurosurgical procedures and permit severe pain in only 1.6% of neurosurgeries through 24 hours post-surgery is surprising and unexpected. There is nothing in the reported and published medical and scientific literature that suggests or teaches the combination of the three MMOSA ingredients from three different drug classes, would return this statistically significant, exemplary, unexpected, and surprising result.

Recently, the Wang reference disclosed that sixty-two patients undergoing total hip arthroplasty with spinal anesthesia were treated with either 13.5 mg hyperbaric Bupivacaine with Normal Saline or 13.5 mg hyperbaric Bupivacaine with 2 mg preservative-free Ketorolac. The results suggest that the pain during the first 2 days after surgery did not differ between the Ketorolac and Saline groups, importantly the postoperative opioid use did not differ between the Ketorolac and Saline groups (Table 2 below). Wang reported the presence and area of hyperalgesia and allodynia surrounding the wound objectively measured at 48 h postoperatively was similar from each differently treated group. Therefore, this peer-reviewed and published literature demonstrated inefficiency and lack of clinical efficacy of Ketorolac to reduce postoperative pain, when it is combined with Bupivacaine, as compared to Bupivacaine alone, clearly teaching that a motivation is lacking, it would be counterintuitive, to combine Ketorolac and Bupivacaine at the time the present invention was discovered. The Wang prior art is also pointing researchers in an opposite direction than the direction of the present invention. In other words, Wang et. al. teaches away from the proposed combination of Bupivacaine, Ketamine and Ketorolac as a multimodal analgesic composition, as claimed in the present invention, to significantly reduce postoperative pain.

In another literature, Rahmanian et al. disclosed the clinical ineffectiveness of Local Infiltrative Bupivacaine in Lumbar Laminectomy. Rahmanian reported that 30 mL of 0.25% Bupivacaine Hydrochloride administered as an infiltrative field block at the time of surgical closure was no more effective than 30 ml Normal Saline in decreasing postoperative surgical pain. Pain was assessed at rest using subjective linear VAS scores. In the Rahmanian prior art, VAS scores in the Bupivacaine group were surprisingly higher than the control Normal Saline group (Table 2 below). The Rahmanian reported findings, compared to those reported using BKK infiltration in the exact same surgical procedure, where BKK was used as an infiltrative anesthetic/analgesic in thousands of surgeries, are disruptive and provide contrary teaching, guiding the student of the art away from the current invention. Table 2 summarizes this discussion.

TABLE 2

PAIN RELIEF POST OPERATIVELY AFTER PAINFUL PROCEDURES

| Formulation | Patients with NO PAIN | Patients with MILD PAIN | Time | Reference | Conclusion |
|---|---|---|---|---|---|
| BKK | 25.4% | 59.4% | 24 hr | Present Invention | The BKK formulation shows a surprising result to reduce postoperative pain. |
| Bupivacaine + Ketorolac intrathecal and intravenous morphine or hydromorphone with subsequent oral oxycodone 24 hr. Postoperative. | 0% | 0% | 24 hr | Wang et al. | Bupivacaine + Ketorolac combination intrathecal is not more effective than Bupivacaine + Saline intrathecal combination in reducing post-operative pain. |
| Bupivacaine Infiltrative Block | 0% | 0% | 12 hr. | Rahmanian et al. | 30 mL of 0.25% Bupivacaine Hydrochloride was no more effective than 30 ml Normal Saline in decreasing postoperative surgical pain. |
| Saline Infiltrative Block | 0% | 0% | | | |

Clearly, one of ordinary skill would not be able to make a projection from Wang and/or Rahmanian, that the combination of Bupivacaine Hydrochloride, Ketamine Hydrochloride, and Ketorolac Tromethamine would result in an anesthetic/analgesic that surprisingly allows NO pain in more than 25% of patients, mild pain in 59.4%, moderate pain in 13.5% and severe pain in only 1.6% of the BKK treated patients 24 hours postoperatively. Wang and Rahmanian published peer reviewed and reported findings that are contradictory to using the BKK formulation of the present invention in the exact same surgical procedure. The exemplary MMOSA formulations herein, such as but not limited to BKK, clearly provide a clinically and statistically significant improvement compared to standard of care that is counterintuitive and disruptive to existing standard of care therapies.

Formulations Comprising Alpha Agonists

The MMOSA formulations are not limited to the aforementioned BKK example. The present invention also features opioid-sparing, analgesic, anesthetic, anti-nociceptive, analgesic, anti-inflammatory formulations comprising a local anesthetic, a cyclooxygenase (COX) inhibitor, and an alpha agonist(s), and methods featuring administration of said opioid-sparing, analgesic, anesthetic, anti-nociceptive, analgesic, anti-inflammatory formulations. For example, the present invention features methods of treating pain (or controlling pain, managing pain, preventing pain, preempting pain) wherein an effective amount of a formulation comprising a local anesthetic, a cyclooxygenase (COX) inhibitor, and an alpha agonist(s) administered to a subject, e.g., a mammal, in need thereof. In some embodiments, administration is by subcutaneous injection, intramuscular injection, interfascial plane injection, rectal injection or retention, intraperitoneal, tumescent, nebulized, passive or active transdermal injection, or intradermal injection.

In some embodiments, the formulation comprises a local anesthetic comprising Bupivacaine Hydrochloride, Ropivacaine Hydrochloride, or Levobupivacaine Hydrochloride, a cyclooxygenase (COX) inhibitor comprising Meloxicam, Ketorolac Tromethamine, Ibuprofen, Acetaminophen, Diclofenac, or Parecoxib, Ketoprofen, Dexketoprofen, Celecoxib, Naproxen, Tolmetin, Carprofen, Etodolac, Fenoprofen, Indomethacin, Diflunisal, or Nabumetone, and an alpha agonist comprising Epinephrine, Clonidine, Phenylephrine, or Dexmedetomidine. In some embodiments, the formulation comprises a local anesthetic comprising Bupivacaine Hydrochloride, Ropivacaine Hydrochloride, Levobupivacaine Hydrochloride, Lidocaine, Prilocaine, Amethocaine, Procaine, Cinchocaine, Mepivacaine, Etidocaine, or Tetracaine (or other long acting local anesthetic); a cyclooxygenase (COX) inhibitor comprising Meloxicam, Ketorolac Tromethamine, Ibuprofen, Acetaminophen, Diclofenac, Parecoxib, Ketoprofen, Dexketoprofen, Celecoxib, Naproxen, Carprofen, Tolmetin, Etodolac, Fenoprofen, Indomethacin, Diflunisal, or Nabumetone (or other parenteral COX inhibitor drug in this class); and an alpha agonist comprising Clonidine or Dexmedetomidine (or other appropriate drug in this class, e.g., Epinephrine)

In some embodiments, the formulation comprises about 0.01%-0.5% of the local anesthetic.

In some embodiments, the formulation comprises about 0.01-3.0 mg/cc of the cyclooxygenase (COX) inhibitor. In some embodiments, the formulation comprises about 0.2-1.2 mg/cc of the COX inhibitor. In some embodiments, the formulation comprises about 0.2-1.5 mg/cc of the COX inhibitor. In some embodiments, the formulation comprises about 0.2-3 mg/cc of the COX inhibitor.

The concentration of the alpha agonist may vary greatly. For example, in an embodiment wherein the formulation is used in tumescent liposuction, one of ordinary skill in the art may opt for a formulation with a higher concentration of alpha agonist such that when diluted in 1 L of fluid, the dilute solution yields a clinically appropriate alpha agonist concentration. In some embodiments, the formulation comprises about 0.1 to 100 micrograms/cc of the alpha agonist. In some embodiments, the formulation comprises about 0.001 to 0.05 mg/cc of the alpha agonist. In some embodiments, the formulation comprises about 0.0025-0.04 mg/cc of the alpha agonist. In some embodiments, the formulation comprises about 0.001-0.06 mg/cc of a second alpha agonist. The present invention is not limited to the aforementioned concentration or concentration ranges. In some embodiments, the alpha agonist is administered as 1-10 micrograms/kg. In some embodiments, the alpha agonist is administered as 0.1-10 micrograms/kg. For example, in some embodiments, the formulation comprises a dose of 0.5 microgram/kg of a second alpha agonist, for example, Dexmedetomidine, Phenylephrine, or Clonidine.

In some embodiments, the MMOSA formulation further comprises one or more additional compositions. For example, the formulation may further comprise Buprenorphine, Dexketoprofen, Carprofen, a N-methyl-D-aspartate (NMDA) receptor antagonist, an antifibrinolytic, an antibiotic, a steroid, a cyclooxygenase 3 inhibitor, a Transient Receptor Potential Vanilloid (TRPV) receptor agonist or antagonist, a Transient Receptor Potential channel agonist or antagonist, a protein kinase inhibitor, a competitive or non-competitive glycine or glutamate agonist, a glutamate or glycine inhibitor, a neurokinin-1 receptor antagonist, a second alpha agonist, or a combination thereof.

As an example, in some embodiments, the MMOSA formulation comprises a local anesthetic, a cyclooxygenase (COX) inhibitor, an alpha agonist(s), and a NMDA receptor antagonist. In some embodiments, the formulation comprises about 0.5-3.0 mg/cc of the NMDA receptor antagonist. In some embodiments, the formulation comprises about 0.01-3.0 mg/cc of the NMDA receptor antagonist.

Table 3 below provides examples of formulations included in the present invention. The present invention is not limited to the formulations disclosed herein.

TABLE 3

Non-limiting examples of MMOSA formulations

| Example | Local Anesthetic | COX Inhibitor | Alpha Agonist | NMDA Receptor Antagonist | Buprenorphine | Dexketoprofen | Antifibrinolytic | Antibiotic | Steroid | COX 3 Inhibitor | TRPV receptor agonist or antagonist | Protein Kinase Inhibitor | Glycine or Glutamate Agonist | Glycine or Glutamate Inhibitor | Neurokinin-1 Receptor Antagonist | Second Alpha Agonist |
|---|---|---|---|---|---|---|---|---|---|---|---|---|---|---|---|---|
| 1 | X | X | X | | | | | | | | | | | | | |
| 2 | X | X | X | X | | | | | | | | | | | | |
| 3 | X | X | X | | | | | | | | | | | | | |
| 4 | X | X | X | | X | | | | | | | | | | | |
| 5 | X | X | X | | | X | | | | | | | | | | |
| 6 | X | X | X | | | | X | | | | | | | | | |
| 7 | X | X | X | | | | | X | | | | | | | | |
| 8 | X | X | X | | | | | | X | | | | | | | |
| 9 | X | X | X | | | | | | | X | | | | | | |
| 10 | X | X | X | | | | | | | | X | | | | | |
| 11 | X | X | X | | | | | | | | | X | | | | |
| 12 | X | X | X | | | | | | | | | | X | | | |
| 13 | X | X | X | | | | | | | | | | | X | | |
| 14 | X | X | X | | | | | | | | | | | | X | |
| 15 | X | X | X | | | | | | | | | | | | | X |
| 16 | X | X | X | X | X | | | | | | | | | | | |
| 17 | X | X | X | X | | X | | | | | | | | | | |
| 18 | X | X | X | X | | | X | | | | | | | | | |
| 19 | X | X | X | X | | | | X | | | | | | | | |
| 20 | X | X | X | X | | | | | X | | | | | | | |
| 21 | X | X | X | X | | | | | | X | | | | | | |
| 22 | X | X | X | X | | | | | | | X | | | | | |
| 23 | X | X | X | X | | | | | | | | X | | | | |
| 24 | X | X | X | X | | | | | | | | | X | | | |
| 25 | X | X | X | X | | | | | | | | | | X | | |
| 26 | X | X | X | | | | X | X | | | | | | | X | |
| 27 | X | X | X | | | | X | X | | | | | | | | X |
| 28 | X | X | X | | | | | X | X | | | | | | | X |
| 29 | X | X | X | X | | | | X | X | | | | | | | |
| 30 | X | X | X | | | | | | X | X | | | | | | |
| 31 | X | X | X | X | | | | X | X | | | | | | | |
| 32 | X | X | X | | | | | X | X | X | | | | | | |
| 33 | X | X | X | X | | | | | X | X | | | | | | |
| 34 | X | X | X | X | | X | | X | | | | | | | | |
| 35 | X | X | X | X | | X | | X | | | | X | | | | |
| 36 | X | X | X | | | | | | X | | | X | | | | |
| 37 | X | X | X | X | | | | X | X | X | | | | | | |
| 38 | X | X | X | X | | | | X | | X | | | | | | |
| 39 | X | X | X | | | | | X | X | | | | | | | |
| 40 | X | X | X | X | | X | X | | | | | | | | | |

In some embodiments, the NMDA receptor antagonist is Magnesium Sulfate, Ketamine (Ketamine Hydrochloride), Trolamine, Tramadol, Ifenprodil, Dextromethorphan, Meperidine, Methadone, Minocycline, Agmatine, or Aptiganel.

In some embodiments, the antifibrinolytic is Tranexamic Acid, Epsilon-aminocaproic acid or other lysine analogue, Aprotinin or other serine protease inhibitor, the like, or a combination thereof. In some embodiments the concentration of Tranexamic Acid is 1 to 10 mg/cc. In some embodiments the concentration of Tranexamic Acid is 1 to 15 mg/cc. In some embodiments the concentration of Tranexamic Acid is 1 to 20 mg/cc. In some embodiments the concentration of Tranexamic Acid is 1 to 25 mg/cc. In some embodiments the concentration of Tranexamic Acid is 5 to 10 mg/cc. In some embodiments the concentration of Tranexamic Acid is 5 to 15 mg/cc. In some embodiments the concentration of Tranexamic Acid is 5 to 20 mg/cc. In some embodiments the concentration of Tranexamic Acid is 5 to 25 mg/cc. In some embodiments the concentration of Tranexamic Acid is 10 to 20 mg/cc. In some embodiments the concentration of Tranexamic Acid is 10 to 25 mg/cc. The present invention is not limited to the aforementioned concentrations and concentration ranges of Tranexamic Acid.

As discussed herein, the formulations may comprise an alpha agonist and optionally a second alpha agonist. In some embodiments, the alpha agonist and/or the second alpha agonist is Clonidine, Dexmedetomidine, Tizanidine, Guanfacine, Medetomidine, Metaraminol, Oxymetazoline, Phenylephrine or Epinephrine.

In some embodiments, the cyclooxygenase 3 inhibitor is Acetaminophen or Paracetamol.

In some embodiments, the steroid is Dexamethasone, Methylprednisolone, Betamethasone, Diprospan (Betamethasone Disodium Phosphate and Betamethasone Dipropionate), a mineralocorticosteroid, or a glucocorticosteroid.

In some embodiments, the antibiotic is a beta lactam antibiotic or Vancomycin. In some embodiments, the antibiotics include Cefazolin, Cephalexin, Cefaclor, Cefuroxime, Ceftibuten, Penicillin V, Nafcillin, Amoxicillin, Ampicillin, or any of the other cephalosporins for penicillinase resistant antibiotics in the class, including beta-lactam inhibitors. In some embodiments, the concentration of the antibiotic is from 1-10 mg/cc. In some embodiments, the concentration of the antibiotic is from 1-20 mg/cc. In some embodiments, the concentration of the antibiotic is from 1-25 mg/cc. In some embodiments, the concentration of the antibiotic is from 1-30 mg/cc. In some embodiments, the concentration of the antibiotic is from 5-20 mg/cc. In some embodiments, the concentration of the antibiotic is from 5-25 mg/cc. In some embodiments, the concentration of the antibiotic is from 5-30 mg/cc. In some embodiments, the concentration of the antibiotic is from 10-20 mg/cc. In some embodiments, the concentration of the antibiotic is from 10-25 mg/cc. In some embodiments, the concentration of the antibiotic is from 10-30 mg/cc. In some embodiments, the concentration of the antibiotic is from 20-30 mg/cc. The present invention is not limited to the aforementioned concentrations or concentration ranges of antibiotics.

In some embodiments, the Transient Receptor Potential channel agonist or antagonist is Magnesium Sulfate, Remacemide, Tiletamine, Capsaicin, Resiniferatoxin, Capsazepine, an aryl urea cinnamide, a carboxamide antagonist, or a vanilloid agonist or antagonist. In some embodiments, the Transient Receptor Potential Vanilloid (TRPV) receptor agonist or antagonist comprises Capsaicin or Resiniferatoxin. The majority of nociceptive transducers are TRP channels converting nociceptive thermal, mechanical, or chemical stimuli to transmitted nociceptive signals. MMOSA formulations with Transient Receptor Potential channel agonists or antagonists provide preventative, preemptive, infiltrative multimodal analgesia modulating cellular and molecular nociceptive mechanisms at the point of surgical trauma.

In some MMOSA embodiments, the protein kinase inhibitor is Temsirolimus, PKA, mTOR, MAPK, PKG, p38 MAPKs, EGFR, PKG, ERK, JAK, a tropomyosin related kinase inhibitor (TrK), BDNF, VEGFR, or a combination thereof.

The MMOSA formulation may be used in any clinically relevant application and at any clinically needed or appropriate time (e.g., during, before, or after a procedure). Non-limiting examples of procedures or applications for the methods and compositions of the present invention include joint procedures, anterior spinal procedures, posterior spinal procedures, Lumbar Discectomies, Decompressive Lumbar Laminectomies, Anterior Cervical Discectomies, Peripheral Nerve Decompressive Procedures, Anterior Lumbar Fusion, Decompressive Laminectomy with/or without instrumentation, Cardiovascular surgery including pacemaker and defibrillator procedures, Colorectal surgery, General surgery, Gynecological and Obstetrical surgery, Neurological surgery, Ophthalmic surgery, Orthopedic surgery, Oral and Maxillofacial surgery, Otolaryngologic surgery, Pediatric surgery, Dental procedures and surgery, Podiatric surgery, Endoscopic surgery, any and all Veterinary surgery or procedures or any minimally invasive surgery or procedure. The present invention is not limited to the aforementioned applications.

A MMOSA formulation may be administered as befitting, including but not limited to after, or before, any surgical incision, laceration, endoscopic post or preoperative port site including, neurosurgical procedures on the cranium, spine, or extremities, including but not limited, to open decompressive procedures on peripheral nerves, spinal nerves and spinal plexuses, or lamina, including fusions and instrumentation. Orthopedic applications include, but are not limited to, open reduction and internal fixation of fractures, closed reduction of fractures and direct injection of associated hematoma, total joint arthroplasty of the shoulder, knee, hip, elbow and ankle. General surgery applications include, but are not limited to, colorectal surgery, hepatobiliary surgery, including robotic laparoscopic assisted or laparoscopic cholecystectomy, appendectomy, colectomy, or hernia repair, other general surgical or colorectal surgeries including hemorrhoidectomy, breast surgeries, excision, biopsy, augmentation or reduction, and amputations of extremities or digits. Cardiothoracaic surgery MMOSA applications include thoracotomy, mediastinal surgery, sternotomy and robotic or video assisted thoracoscopy. Otolaryngological MMOSA applications include, but are not limited to, dental and maxillofacial surgery, including surgeries on the neck and throat, ear surgery, thyroid and parathyroid surgery, tonsillectomy, adenoidectomy, laryngectomy, third molar extraction, temporomandibular joint surgery, other dental extraction or endodontic, and dental implant surgery. Obstetrical, Gynecological and Women's Health surgery applications include, but are not limited to, hysterectomy, oophorectomy, C-section, robotic assisted and/or laparoscopic or laparotomy surgery. Podiatric MMOSA applications include, but are not limited to, bunionectomy, forefoot surgery, hind foot surgery, plantar surgery, or foot or ankle joint arthroplasty. The present invention is not limited to any of the aforementioned procedures or applications.

The MMOSA formulation may be administered as practical, timely, indicated, and appropriate. In some MMOSA embodiments, the MMOSA formulation is injected, infiltrated, instilled, or irrigated, via a basin, other vessel, pump or syringe. In some MMOSA embodiments, the MMOSA formulation is injected as a tumescent or intraperitoneal injection. In some embodiments, the MMOSA formulation is administered with an active transdermal delivery system. An example of such is disclosed in WO2009046345A1, the disclosure of which is incorporated herein by reference in its entirety. In some embodiments, the formulation is administered to a site prior to a needle insertion or an incision. In some MMOSA embodiments and applications, MMOSA is delivered by standard nebulization or vibrating mesh nebulizer. The present invention is not limited to the aforementioned modes, routes, or methods of administration.

Manufacturing and Packaging

The formulations of the present invention may be manufactured and packaged using a variety of methods, and packaged in a variety of forms. For example, in some embodiments, the MMOSA formulations are packaged in liquid form in a container such as, but not limited to, a sterile syringe, a blow-fill-seal vessel. In some embodiments, the MMOSA formulations are packaged in separate containers in their clinically useful concentrations. In some embodiments, the formulations are packaged in separate or single containers in a concentrated form with the expectation for clinical use, the formulations will be combined with another solution (e.g., normal saline) to achieve the appropriate clinically useful concentration. For example, the contents of a container (in concentrated form) can be translocated to a sterile basin on the sterile surgical field, normal saline added to reach the final clinically useful concentration.

In some embodiments, a volume of a concentrated cGMP MMOSA formulation is packaged in a sterile container (e.g., blow-fill-seal vessel). In some embodiments, the volume is 10 cc. In some embodiments, the volume is 15 cc. In some embodiments, the volume is 20 cc, 30 cc, 40 cc, 50 cc, 60 cc, 70 cc, 80 cc, 90 cc. In some embodiments, the volume is 100 cc, 150 cc, or more.

In some embodiments, a volume of a non-concentrated MMOSA formulation is packaged in a container (e.g., blow-fill-seal vessel). In some embodiments, the volume is 50 cc. In some embodiments, the volume is 0.5 cc or less. In some embodiments, the MMOSA formulation volume is 60 cc, 70 cc, 80 cc, 90 cc, 100 cc or more.

In some embodiments, the MMOSA formulations are packaged in solid form, e.g., one or more of the components of the formulation is lyophilized. In some embodiments, lyophilization of one or more of the components may help appreciably extend the shelf life of the MMOSA formulation, and enhance safety, convenience, and storage (among other things) of the MMOSA formulation. In some embodiments, the MMOSA formulation is a lyophilized formulation, or sterile liquid, comprising Ropivacaine Hydrochloride 0.25% as the amide local anesthetic, Ketamine Hydrochloride 1.0 mg/cc as the NMDA receptor antagonist, Ketorolac Tromethamine 1.0 mg/cc as the COX inhibitor, Epinephrine 5 micrograms/cc as an alpha agonist, Dexmedetomidine 1.0 microgram/cc as a second alpha agonist, Capsaicin 0.25% as the TRPV channel agonist, Cefazolin 7.5 mg/cc as the antibiotic, and Tranexamic acid 5 mg/cc as the antifibrinolytic. The lyophilized formulation may have a prolonged and extended beyond use date critical for third world, battlefield, and catastrophic applications like earthquakes, tsunami, hurricanes, tornados, floods, and other manmade or natural disasters.

The present invention is not limited to the particular features of manufacturing and/or packaging disclosed herein. For example, while the above describes packaging the formulations as single compositions, in some embodiments, the formulations may be packaged as two, three, or more separate compositions to be combined or admixed prior to use, as an example, translocating and admixing on the surgical field.

The present invention is not limited to the specific recited applications disclosed herein. For example, in some MMOSA embodiments, the MMOSA formulation is utilized in veterinary applications including but not limited to those that are similar or exact applications recited in humans. In some embodiments, the MMOSA formulation is administered to animals such as dogs, cats, horses, rabbits, or other mammals. In some embodiments, the MMOSA formulation is utilized in dental applications. For example, in MMOSA infiltration conducive to relieving the pain from an extraction, the MMOSA formulation may be injected to a patient's gums prior to or after extracting a tooth or performing painful dental procedures providing multimodal opioid free anti-emetic analgesia.

The present invention is not limited to the precise and specific MMOSA formulations recited and disclosed herein. A clinician with experience, knowledge, and abreast of the current art would recognize minor but still clinically effective changes to a MMOSA formulation component would notwithstanding teach a clinically effective formulation and understanding the doctrine of equivalents would retain, possess, and impart those clinical benefits taught herein.

Example 1

The following is a non-limiting example of the present invention. It is to be understood that said example is not intended to limit the present invention in any way. Equivalents or substitutes are within the scope of the present invention.

The following is a non-limiting example of administering said MMOSA formulation to a patient requiring surgery, for example, Decompressive Lumbar Laminectomy with Fusion:

Preoperative Period

1. The patient is injected at or near the surgical site (thoracolumbar, erector spinae plane, or other fascial plane) with 5 to 60 ccs of the MMOSA formulation 15 to 30 minutes prior to the surgical procedure, or alternatively, at wound closure. The injection may be guided using direct vision or endoscopic assisted identification of anatomic landmarks, ultrasound, electrical stimulation, or x-ray.

Perioperative Period

2. The patient is injected with 5 to 120 cc of the MMOSA formulation as an infiltrative field block or fascial plane block prior to surgical incision, or more routinely, at the time of wound closure.

Postoperative Period

3. The patient is administered a continuous infusion of the MMOSA formulation delivered through a catheter system incorporated into the tissue adjacent to the surgical incision or placed into or adjacent to a fascial plane. For example, an erector spinae plane block with a continuous infusion via direct placement of anatomically localized maintained and strategically placed catheter(s).

Example 2

The following is a non-limiting example of the present invention. It is to be understood that said example MMOSA formulation is not intended to limit the present invention in any way. Equivalents or substitutes are within the scope of the present invention.

The following provides non-limiting examples of MMOSA formulation preparation.

In one example, the MMOSA formulation is prepared following USP 797/800 guidelines in a 60 cc sterile syringe, final component admixture formulation: 30 cc 0.25% Bupivacaine Hydrochloride with 1:400,000 Epinephrine, 1.0 mg/cc Ketorolac Tromethamine, and 1 mg/cc of Ketamine Hydrochloride diluted with preservative free sterile Normal Saline to 60 cc final volume: (1) Following USP 797/800 guidelines for (non-inordinate) repetitive compounding of complex sterile admixtures, for a single prescribed patient: Dilute 30 cc of 0.5% Bupivacaine Hydrochloride with Epinephrine 1:200,000, admixed and diluted with, 27.4 cc preservative free Normal Saline (NS); (2) Admix 2.0 ml of Ketorolac Tromethamine 30 mg/cc; (3) Admix 0.6 ml of Ketamine Hydrochloride 100 mg/cc. Final admixture volume is 60 cc. The MMOSA formulation can also be prepared in a 50 cc volume with required change in the Normal Saline dilutant volume maintaining similar final formulation concentrations as in the recited 60 cc volume formulation. A student of the art would also comprehend using an alternative amide local anesthetic, alternative concentrations of an amide local anesthetic, Ketamine Hydrochloride, or alternative in class, Ketorolac Tromethamine, or alternative in class, would result in similar and clinically effective final components and concentrations that are clinically efficacious and clinically equivalent to the exemplary formulation, or in a different final volume.

In one MMOSA formulation example, the analgesic formulation is prepared in a 60 cc syringe containing 0.25% Bupivacaine Hydrochloride, 0.6 mg/ml Ketorolac Tromethamine, and 1 mg/ml of Ketamine Hydrochloride: (1) Following USP 797/800 guidelines (for non-inordinate preparation of complex compounded admixtures), for a single prescribed patient: Admix 30 cc of 0.5% Bupivacaine Hydrochloride with 1; 200,000 Epinephrine with 28.2 cc preservative free Normal Saline (NS); (2) Add 1.2 ml of Ketorolac Tromethamine 30 mg/cc; (3) Add 0.6 ml of Ketamine Hydrochloride 100 mg/cc.

In some embodiments the MMOSA formulation comprises Ropivacaine Hydrochloride 0.25% with Epinephrine 1; 200,000, or 1:400,000 as an alpha agonist, Ketorolac Tromethamine 0.3 to 1 mg/cc, and dexmedetomidine 1-10 micrograms/cc as an alpha agonist. In some embodiments the MMOSA formulation comprises Bupivacaine Hydrochloride as the amide local anesthetic in a concentration of 0.1 to 0.5 mg/cc, or Levobupivacaine Hydrochloride 0.1 to 0.5 mg/cc. In some MMOSA formulation embodiments, the alpha agonist is clonidine 1-10 micrograms/cc and the COX inhibitor is Meloxicam 0.02 to 1 mg/cc. The present invention is not limited to these particular MMOSA formulations nor the others disclosed herein.

Example 3

The following is a non-limiting example of the present MMOSA invention. It is to be understood, intuitively obvious to those schooled in the art, that said example is not intended, would not, limit the present MMOSA invention in any way. Clinically relevant substitutions or equivalents or drug class substitutes are within the scope of the present invention.

The following provides non-limiting examples of aspects of administration of MMOSA formulations.

In some embodiments, the MMOSA formulation is administered between about every 6 to 12 hours until the pain completely subsides. In some embodiments, the MMOSA formulation is administered between about every 10 to 16 hours until the pain completely subsides. In some embodiments, the MMOSA formulation is administered, then repeated, between about every 12 to 24 hours, or longer, until the pain is effectively controlled.

In some embodiments, for clinical purposes, the volume of the MMOSA formulation used as a single infiltration may vary from between about 0.1 ml to 1000 ml, as in tumescent infiltration.

In some embodiments, the MMOSA formulation is administered preemptively at or adjacent to the sites of nociception to provide preventative pain relief. In some embodiments, the MMOSA formulation is administered once a day, for example, for fast, extended pain relief or more frequently, such as twice or three times a day, to maintain pain relief. MMOSA formulations used as a single infiltration or continuous infiltration may vary from a single infiltration of 1-100 cc to 1000 cc per day as a continuous infusion delivered by an elastomeric or electronic pump or cassette driver. In some embodiments, the volume of the MMOSA formulation used as a single infiltration may vary from between about 3 cc (e.g., for a dental procedure) to 1000 cc, for tumescent analgesia, intraperitoneal infiltration, liposuction, or hair transplants. for example. In some embodiments, the volume of the MMOSA formulation used as a single infiltration may vary from between about 500 to 1000 cc. In some embodiments, the volume of the MMOSA formulation used as a single infiltration may vary from between about 0.1 to 100 cc. In some embodiments, the volume of the MMOSA formulation used as a single infiltration may vary from between about 0.1 to 60 cc. The MMOSA formulation may be delivered to the surgical site by single injections or through continuous infiltration catheters anatomically placed and/or guidance directed prior to surgery, during surgery, or after surgery, delivered intraperitoneal, or at surgical wound closure, allowing the formulation to be delivered to the surgical site or fascial plane containing nerves that innervate the surgical site.

In some embodiments, the MMOSA formulation may be delivered as a continuous infusion/infiltration for delivering the MMOSA formulation to targeted nociceptors, including muscle, soft tissue including skin, subcutaneous tissue and fat, fascial planes, bone, periosteum, intraperitoneal infiltration, and peripheral sensory nerves. In some embodiments, continuous infusion rates of the formulation vary from 1.0 mL to 100 mL per hour. In some embodiments, continuous infusion rates of the formulation vary from 1.0 cc to 10 cc per hour, for example, ophthalmic enucleation. In some embodiments, continuous infusion rates of the formulation vary from 10 cc to 50 cc per hour. In some embodiments, continuous infusion rates of the formulation vary from 50 cc to 100 cc per hour. In some embodiments, the formulation is administered intradermally, intranasally, active, or passive transdermal, nebulized, rectally, or subcutaneously, using a needle, catheter, and/or syringe. Alternatively, a vibrating mesh nebulizer can deliver MMOSA to the upper airway, intraoral tissues, intranasal tissues, and the pulmonary circulation. The present invention is not limited to any of the specific modes or mechanisms of delivery.

In some embodiments, the MMOSA formulation is used at any surgical or traumatic site on/in the body where nociception reduction is required or desirable. In some embodiments, the MMOSA formulation is used to reduce or eliminate nociceptive pain, other than somatic or neuropathic pain. In some embodiments, the MMOSA formulation can be used in remote, battlefield, or third world applications where other analgesia or anesthesia options are too complicated, expensive, or simply unavailable. MMOSA may be used to treat pain caused by injuries, such as wounds and burns, at/in facilities where medical procedures, advanced trauma life support, dental procedures, obstetrical procedures, veterinary procedures, and cosmetic or reconstructive procedures (cleft lip, cleft palate) are performed. For example, the MMOSA formulation may be administered to a patient having an abrasion, cut, puncture wound, incision, hematoma, fracture, or other skin or soft tissue wound or injury that causes pain. As another example, thermal injuries cause pain and administering the MMOSA formulation administered topically or infiltrated would rapidly reduce the pain associated with thermal injuries.

The volume of the formulation may be determined by a patient's weight and the required clinically effective minimal concentration of the formulation. In a non-limiting example, the required effective minimal concentration of the MMOSA formulation components may be 0.048 to 0.5% of the local anesthetic, 0.12 mg/kg to 3 mg/kg of the N-methyl-D-aspartate (NMDA) receptor antagonist, and 0.4 mg/kg to 1.5 mg/kg of the cyclooxygenase (COX) inhibitor. In some embodiments, the alpha agonist concentration is from 0.001 to 0.5 mg/cc, 1 to 10 micrograms/kg. As a non-limiting example, a patient weighing 160 pounds, or 72.7 kgs, and having a lumbar spinal procedure may safely be administered 60 cc of the exemplary concentrations of MMOSA; 0.25% Bupivacaine Hydrochloride with or without Epinephrine, 1 mg/cc Ketorolac Tromethamine, and 1 mg/cc Ketamine Hydrochloride, and 0.001 to 0.05 mg/cc, 0.1 to 10 micrograms/cc of an alpha agonist. In some embodiments, the alpha agonist is 2.5 micrograms/cc. In some embodiments, the alpha agonist is 1:200,000, 1:400,000 (or a range therein), e.g., epinephrine.

As used herein, the term "about" refers to plus or minus 10% of the referenced number.

Various modifications of the invention, in addition to those described herein, will be apparent to those skilled in the art from the foregoing description. For example, examples including but not limited to those described in US 2009/0093669 A1 and WO2009046345A1, the disclosures of which are incorporated herein by reference in their entirety, may be applied to enable the invention to administer through active transdermal delivery. Such modifications are also intended to fall within the scope of the appended claims. Each reference cited in the present application is incorporated herein by reference in its entirety.

Although there has been shown, recited, and described the preferred embodiment of the present invention, it will be readily apparent to those skilled in the art that modifications may be made thereto which do not exceed the scope of the appended claims. Therefore, the scope of the invention is only to be limited by the following claims. In some embodiments, descriptions of the inventions described herein using the phrase "comprising" includes embodiments that could be described as "consisting essentially of" or "consisting of," and as such the written description requirement for claiming one or more embodiments of the present invention using the phrase "consisting of" is met.

What is claimed:

1. A composition for treating pain and for administering by subcutaneous injection, intramuscular injection, interfascial plane injection, transdermal delivery, tumescent or intraperitoneal or intradermal injection, the composition comprising:
    a. about 0.01%-0.5% of a local anesthetic comprising Bupivacaine Hydrochloride;
    b. about 0.01-3.0 mg/cc of an N-methyl-D-aspartate (NMDA) receptor antagonist comprising Ketamine Hydrochloride;
    c. about 0.01-1.5 mg/cc of a cyclooxygenase (COX) inhibitor comprising Carprofen; and
    d. a Transient Receptor Potential Vanilloid (TRPV) receptor agonist comprising Vocacapsaicin.

\* \* \* \* \*